US009585878B2

(12) United States Patent
Hayardeny

(10) Patent No.: US 9,585,878 B2
(45) Date of Patent: Mar. 7, 2017

(54) TREATMENT OF BDNF-RELATED DISORDERS USING LAQUINIMOD

(75) Inventor: Liat Hayardeny, Tel Aviv (IL)

(73) Assignee: TEVA PHARMACEUTICAL INDUSTRIES, LTD., Petach-Tikva (IL)

( * ) Notice: Subject to any disclaimer, the term of this patent is extended or adjusted under 35 U.S.C. 154(b) by 892 days.

(21) Appl. No.: 12/806,275

(22) Filed: Aug. 9, 2010

(65) Prior Publication Data
US 2011/0034508 A1   Feb. 10, 2011

Related U.S. Application Data

(60) Provisional application No. 61/273,920, filed on Aug. 10, 2009.

(51) Int. Cl.
| | | |
|---|---|---|
| A61K 31/47 | (2006.01) | |
| A61K 9/48 | (2006.01) | |
| A61K 31/4704 | (2006.01) | |
| A61K 31/138 | (2006.01) | |
| A61K 31/428 | (2006.01) | |
| A61K 9/00 | (2006.01) | |

(52) U.S. Cl.
CPC ........ *A61K 31/4704* (2013.01); *A61K 9/0053* (2013.01); *A61K 31/138* (2013.01); *A61K 31/428* (2013.01)

(58) Field of Classification Search
None
See application file for complete search history.

(56) References Cited

U.S. PATENT DOCUMENTS

| | | | |
|---|---|---|---|
| 3,024,257 A | 3/1962 | Millar et al. | |
| 4,107,310 A | 8/1978 | Allais et al. | |
| 4,547,511 A | 10/1985 | Eriksoo et al. | |
| 4,628,053 A | 12/1986 | Fries et al. | |
| 4,738,971 A | 4/1988 | Eriksoo et al. | |
| 5,716,638 A | 2/1998 | Touitou | |
| 5,912,349 A | 6/1999 | Sih | |
| 6,077,851 A * | 6/2000 | Bjork et al. | 514/312 |
| 6,121,287 A | 9/2000 | Bjork et al. | |
| 6,133,285 A | 10/2000 | Bjork et al. | |
| 6,307,050 B1 | 10/2001 | Kwiatkowski et al. | |
| 6,395,750 B1 | 5/2002 | Hedlund et al. | |
| 6,593,343 B2 | 7/2003 | Bjork et al. | |
| 6,605,616 B1 | 8/2003 | Bjork et al. | |
| 6,696,407 B1 * | 2/2004 | Longo et al. | 514/1 |
| 6,802,422 B2 | 10/2004 | Kalvelage et al. | |
| 6,875,869 B2 | 4/2005 | Jansson | |
| 7,485,311 B2 | 2/2009 | Lue et al. | |
| 7,560,100 B2 * | 7/2009 | Pinchasi et al. | 424/78.17 |
| 7,560,557 B2 | 7/2009 | Jansson | |
| 7,589,208 B2 | 9/2009 | Jansson et al. | |
| 2002/0173520 A1 | 11/2002 | Bjork et al. | |
| 2003/0087929 A1 | 5/2003 | Kimura et al. | |
| 2003/0119826 A1 | 6/2003 | Manning et al. | |
| 2003/0124187 A1 | 7/2003 | Mention et al. | |
| 2004/0247673 A1 | 12/2004 | Fergione et al. | |
| 2005/0074451 A1 | 4/2005 | Yednock et al. | |
| 2005/0192315 A1 | 9/2005 | Jansson et al. | |
| 2005/0215586 A1 | 9/2005 | Jansson et al. | |
| 2005/0271717 A1 | 12/2005 | Berchielli et al. | |
| 2006/0004019 A1 | 1/2006 | Lieberburg | |
| 2007/0086979 A1 | 4/2007 | Chevrier et al. | |
| 2007/0088050 A1 | 4/2007 | Frenkel et al. | |
| 2007/0207141 A1 | 9/2007 | Lieberburg | |
| 2007/0231319 A1 | 10/2007 | Yednock | |

(Continued)

FOREIGN PATENT DOCUMENTS

| | | |
|---|---|---|
| EP | 1073639 | 11/2002 |
| EP | 1097139 | 12/2002 |

(Continued)

OTHER PUBLICATIONS

Katoh-Semba et al., The FASEB J., vol. 16, pp. 1328-1330, Aug. 2002.*
Molteni, Int. J. Neuropsychopharm., (2006), 9, 307-317.*
Chen et al. (2009) "Recent Advances in the Treatment of Amyotrophic Lateral Sclerosis . . . " Central Nervous System Agents in Medicinal Chemistry (9):31-39.*
Hu and Russek (2008) "BDNF and the diseased nervous system: a delicate balance between 3 adaptive and pathological processes of gene regulation" J. of Neurochemistry (105):1-17.*
Chen et al., Kynurenine pathway metabolites in humans: disease and healthy states, Int. J. Tryptophan Res., 2009, 2: 1-19.*
Polman et al., Treatment with laquinimod reduces development of active MRI lesions in relapsing MS, Neurology, 2005; 64: 987-91.*

(Continued)

*Primary Examiner* — Svetlana M Ivanova
(74) *Attorney, Agent, or Firm* — John P. White; Gary J. Gershik; Cooper & Dunham LLP

(57) ABSTRACT

This application provides for a method of increasing brain-derived neurotrophic factor (BDNF) serum level in a human subject comprising periodically administering to the subject an amount of laquinimod or pharmaceutically acceptable salt thereof effective to increase BDNF serum level in the human subject. The method can further comprise periodically administering to the subject an amount of a second BDNF-increasing agent. This application also provides for a method for treating a human subject suffering from a BDNF-related disease comprising periodically administering laquinimod or a pharmaceutically acceptable salt thereof in an amount effective to treat the human subject. This application additionally provides for use of laquinimod in the manufacture of a medicament for increasing BDNF serum level in a human subject. This application further provides for a pharmaceutical composition comprising an amount of laquinimod effective for use in increasing BDNF serum level in a human subject. This application also provides for a pharmaceutical preparation comprising an amount of laquinimod and an amount of a second BDNF-increasing agent effective for use in increasing BDNF serum level in a human subject.

10 Claims, 37 Drawing Sheets

(56) References Cited

U.S. PATENT DOCUMENTS

| | | |
|---|---|---|
| 2007/0280891 A1 | 12/2007 | Tamarkin et al. |
| 2007/0293537 A1 | 12/2007 | Patashnik et al. |
| 2008/0044382 A1 | 2/2008 | Liebergurg et al. |
| 2008/0063607 A1 | 3/2008 | Tamarkin et al. |
| 2008/0090897 A1* | 4/2008 | Steiner et al. ............. 514/453 |
| 2008/0118553 A1* | 5/2008 | Frenkel et al. ............. 424/451 |
| 2008/0166348 A1 | 7/2008 | Kupper et al. |
| 2009/0048181 A1 | 2/2009 | Schipper et al. |
| 2009/0062330 A1* | 3/2009 | Kalafer et al. ............. 514/303 |
| 2009/0081259 A1 | 3/2009 | Jonas et al. |
| 2009/0148462 A1 | 6/2009 | Chevrier et al. |
| 2009/0156542 A1 | 6/2009 | Purschke et al. |
| 2009/0162432 A1 | 6/2009 | Safadi et al. |
| 2009/0221575 A1 | 9/2009 | Gerber et al. |
| 2009/0232889 A1 | 9/2009 | Jansson et al. |
| 2010/0055072 A1 | 3/2010 | Gant et al. |
| 2010/0158903 A1 | 6/2010 | Smith et al. |
| 2010/0260716 A1 | 10/2010 | Stohr et al. |
| 2010/0310547 A1 | 12/2010 | Soliven |
| 2011/0112141 A1 | 5/2011 | Frenkel et al. |
| 2011/0118308 A1 | 5/2011 | Frenkel et al. |
| 2011/0217295 A1 | 9/2011 | Haviv et al. |
| 2011/0218179 A1 | 9/2011 | Haviv et al. |
| 2011/0218203 A1 | 9/2011 | Kaye et al. |
| 2011/0251235 A1 | 10/2011 | Patashnik et al. |
| 2012/0010238 A1 | 1/2012 | Piryatinsky et al. |
| 2012/0010239 A1 | 1/2012 | Fristedt |
| 2012/0142730 A1 | 6/2012 | Tarcic et al. |
| 2012/0225124 A1 | 9/2012 | Safadi et al. |
| 2013/0096158 A1 | 4/2013 | Hallak et al. |
| 2013/0272996 A1 | 10/2013 | Tarcic et al. |

FOREIGN PATENT DOCUMENTS

| | | |
|---|---|---|
| EP | 1095021 | 9/2003 |
| EP | 1511732 | 3/2005 |
| EP | 1720531 | 11/2006 |
| WO | WO 99/55678 | 11/1999 |
| WO | WO 00/03991 | 1/2000 |
| WO | WO 00/03992 | 1/2000 |
| WO | WO 03/106424 | 12/2003 |
| WO | WO 2005/074899 | 8/2005 |
| WO | WO 2007/047863 | 4/2007 |
| WO | WO 2007/139887 | 12/2007 |
| WO | WO 2007/146248 | 12/2007 |
| WO | WO 2008/079270 | 7/2008 |
| WO | WO 2009/082471 | 7/2009 |

OTHER PUBLICATIONS

Sandberg-Wollhelm et al., 48-week open safety study with a high-dose oral laquinimod in MS patients, Abstractverwaltung AKM AG, Sep. 30, 2005.*
Chen et al., Recent advances in the treatment of amyotrophic lateral sclerosis. Emphasis on kynurenine pathway inhibitors, Cent Nerv Syst Agents Med Chem. Mar. 2009;9(1):32-9.*
U.S. Appl. No. 12/804,795, filed Jul. 29, 2010, Tarcic et al.
U.S. Appl. No. 12/803,121, filed Jun. 18, 2010, Tarcic et al.
Written Opinion of the International Searching Authority issued Oct. 5, 2010 in connection with PCT International Application No. PCT/US2010/02194, filed Aug. 9, 2010.
PCT International Search Report issued Oct. 5, 2010 in connection with PCT International Application No. PCT/US2010/02194, filed Aug. 9, 2010.
Acheson, A. et al. (1995) "A BDNF autocrine loop in adult sensory neurons prevents cell death". Nature. 374(6521):450-3.
Alonso, M, et al. (2005) "Endogenous BDNF is required for long-term memory formation in the rat parietal cortex". Learning & Memory. 12:504-510.
Amaral, MD, et al. (2007) "Transient receptor potential channels as novel effectors . . . for Rett syndrome". Pharmacol Ther. 113(2):394-409.
Caffe Romeo, A. et al. (2001) "A combination of CNTF and BDNF rescues rd photoreceptors but changes rod . . . " Investigative Ophthalmology & Visual Science. 42:275-82.
Chesselet, MF (2003) "Dopamine and Parkinson's disease: is the killer in the house?" Molecular Psychiatry. 8:369-370.
Ciammola, A, et al. (2007) "Low brain-derived neurotrophic factor (BDNF) levels in serum of Huntington's disease patients". Am J Med Gent Part B. 144b:574-577.
ClinicalTrials.gov. Bethesda : National Library of Med. updated Jun. 21, 2010, Available from: www.clinicaltrials.gov/ct2/show/NCT00737932?term=Crohns&recr=Open&rank=2.
Howells, DW, et al. (2000) "Reduced BDNF mRNA expression in the Parkinson's disease substantia nigra". Experimental Neurology, 166(1):127-135.
Huang, EJ and Reichardt, LF (2001) "Neurotrophins: roles in neuronal development and function". Annu. Rev. Neurosci. 24:677-736.
Hyman, C. et al., (1991) "BDNF is a neurotrophic factor for dopaminergic neurons of the substantia nigra". Nature. 350(6315):230-2.
Katoh-Semba, R, et al. (2002) "Riluzole enhances expression of brain-derived neurotrophic factor with . . . " FASEB J: 16:1328-30.
Makar, et al. (2008) "Brain derived neurotrophic factor treatment reduces inflammation and . . . " Journal of the Neurological Sciences. 270(1-2):70-76.
Mix, et al. (2008) "Animal models of multiple sclerosis for the development and validation of novel therapies—potential and limitations." Journal of Neurology. 255(6):7-14.
Molteni, R, et al. (2006) "Abstract: Chronic treatment with fluoxetine [Prozac®] up-regulates cellular BDNF mRNA . . . ". Int J Neuropsychopharmacol. 9(3):307-17.
Monteggia, LM (2007) "Elucidating the role of brain-derived neurotrophic factor in the brain". Am J Psychiatry. 164:1790.
Riviere, M. (1998) "An analysis of extended survival in patients with amyotrophic lateral sclerosis treated with riluzole". Arch Neurol. 55:526-8.
Sen, S, et al. (2008) "Serum brain-derived neurotrophic factor, depression, and antidepressant medications: meta-analyses and implications". Biol Psychiatry. 64:527-532.
Snider, et al. (1989) "Neurotrophic molecules". Ann Neurol. 26(4):489-506.
Teva Press Release, "Laquinimod Demonstrated Significant and Sustained Impact on Multiple Sclerosis Disease Activity", Sep. 18, 2008.
Tramontina, JF, et al. (2009) "Brain-derived neurotrophic factor serum levels before and after treatment for acute mania". Neuroscience Letters. 452:111-3.
U.S. Appl. No. 13/560,851, filed Jul. 27, 2012, Gilgun and Tarcic.
U.S. Appl. No. 13/560,872, filed Jul. 27, 2012, Gilgun and Tarcic.
U.S. Appl. No. 13/568,940, filed Aug. 7, 2012, Patashnik et al.
PCT International Search Report issued Apr. 12, 2011 in connection with PCT International Application No. PCT/US2011/26879, filed Mar. 2, 2011.
PCT International Search Report issued Apr. 29, 2011 in connection with PCT International Application No. PCT/US11/26885, filed Mar. 2, 2011.
PCT International Search Report issued May 19, 2011 in connection with PCT International Application No. PCT/US11/26891, filed Mar. 2, 2010.
PCT International Search Report issued Apr. 3, 2012 in connection with PCT/US2011/063460, filed Dec. 6, 2011.
PCT International Preliminary Report on Patentability issued Dec. 20, 2011 in connection with PCT International Application No. PCT/US2010/001759, filed Jun. 18, 2010.
PCT International Preliminary Report on Patentability issued Feb. 14, 2012 in connection with PCT International Application No. PCT/US2010/002194.
Written Opinion of the International Searching Authority issued Apr. 12, 2011 in connection with PCT International Application No. PCT/US2011/26879, filed Mar. 2, 2010.
Written Opinion of the International Searching Authority issued Apr. 29, 2011 in connection with PCT International Application No. PCT/US11/26885, filed Mar. 2, 2010.

(56) References Cited

OTHER PUBLICATIONS

Written Opinion of the International Searching Authority issued May 19, 2011 in connection with PCT International Application No. PCT/US11/26891, filed Mar. 2, 2010.
Written Opinion of the International Searching Authority issued Apr. 3, 2012 in connection with PCT/US2011/063460, filed Dec. 6, 2011.
Office Action issued by the U.S. Patent and Trademark Office on Dec. 27, 2011 in connection with U.S. Appl. No. 12/803,121.
Amendment in Response to Dec. 27, 2011 Office Action filed with the U.S. Patent and Trademark Office on May 29, 2012 in connection with U.S. Appl. No. 12/803,121.
Final Office Action issued by the U.S. Patent and Trademark Office on Jul. 12, 2012 in connection with U.S. Appl. No. 12/803,121.
Barkhof F. (1999) "MRI in Multiple Sclerosis: Correlation with Expanded Disability Status Scale (EDSS)", Multiple Sclerosis. 5(4):283-286.
Boneschi et al. (2003) "Effects of glatiramer acetate on relapse rate and accumulated disbility in multiple sclerosis . . . " Mutt. Scler. 9(4): 349-355.
Comi et al. (2007) LAQ/5062 Study Group. "The Effect of Two Doses of Laquinimod . . . " Presented at: 59th Annual Meeting of the American Academy of Neurology 2007 MA.
De Stefano et al. (1999) "Evidence of early axonal damage in patients with multiple sclerosis", Arch Neurol. 2001;58:65-70.
EMEA Guideline on Clinical Investigation of Medicinal Products for the Treatment of Multiple Sclerosis (CPMP/EWP/561/98 Rev, 1, Nove.2006).
Hohifeld et al. (2000) "The neuroprotective effect of inflammation . . . ", J. Neuroimmunol. 107(2000):161-166.
Karussis et al. (1996) "Treatment of secondary progressive multiple sclerosis with the immunomodulator linomide . . . " Neurology 1996 47(2):341-6.
Lehmann et al. (1997) "Ihibition of the progression of multiple sclerosis by linomide . . . "Clin. Immunol. Immunopathol. Nov. 1997; 85(2):202-9.
Miki, Y, et al. (1999) "Relapsing-Remitting Multiple Sclerosis: Longitudinal Analysis of MR Images—Lack of Correlation between Changes in T2 . . . "Radiology 213:395-399.
Neuhaus et al. (2003) "Immunomodulation in multiple sclerosis: from immunosuppression to neuroprotection", Trends Pharmacol Sci. 24:131-138.
Noseworthy JH, Lucchinetti C, Rodriguez M, Weinshenker BO. (2000) "Multiple sclerosis", N Engl J Med. 343:938-952.
Polman et al., (2005) "Diagnostic criteria for multiple sclerosis: 2005 revisions to the McDonald Criteria", Annals of Neurology, vol. 58 Issue 6, pp. 840-846.
Polman et al., (2005) "Treatment with laquinimod reduces development of active MRI lesions in relapsing MS", Neurology. 64:987-991.
Preiningerova (2009) "Oral laquinimod therapy in relapsing multiple sclerosis", Expert Opinion on Investigational Drugs 18(7):985-989.
Rudick R. (1999) "Disease-Modifying Drugs for Relapsing-Remitting Multiple Sclerosis and Future Directions for Multiple Sclerosis Therapeutics", Neurotherpatueics. 56:10.
Sandberg-Wollheim et al. (2005) "48-Week Open Safety Study with a High-Dose Oral Laouinimod . . . " Ther.-Immunomodulation—Part II, Sep. 30, 2005, 15:30-17:00 (Abstract).
Tuvesson et al. (2005) "Cytochrome P450 3A4 is the Major Enzyme Responsible for the Metabolism of Laquinimod . . . " Drug Metabolism and Disposition. 33(6):866-872.
Extended European Search Report issued Dec. 7, 2012 in connection with European Applicaiton No. 10808442.7.
Hu and Russek (2008) "BDNF and the diseased nervous system: a delicate balance between adaptive and patholigical processes of gene regulation" J. of Neurochemistry (105):1-17.
U.S. Appl. No. 13/757,004, filed Feb. 1, 2013, Tarcic et al.
U.S. Appl. No. 13/768,919, filed Feb. 15, 2013, Ioffe et al.
U.S. Appl. No. 13/800,047, filed Mar. 13, 2013, Kaye.
U.S. Appl. No. 13/874,537, filed May 1, 2013, Bar-Zohar.
U.S. Appl. No. 13/888,709, filed May 7, 2013, Laxer and Ulanenko.
U.S. Appl. No. 13/938,733, filed Jul. 10, 2013, Sarfati et al.
U.S. Appl. No. 13/939,306, filed Jul. 11, 2013, Kaye and Tarcic.
Sep. 20, 2012 Supplementary European Search Report issued in connection with European Patent Application No. 10 78 9873.
Apr. 16, 2013 Response to Sep. 20, 2012 Supplementary European Search Report issued in connection with European Patent Application No. 10 78 9873.
PCT International Preliminary Report on Patentability issued Jun. 12, 2013 in connection with PCT/US11/063460.
Oct. 3, 2012 Examiners Report issued by the New Zealand Patent Office in connection with New Zealand Patent Application No. 597378.
"Guidance for Industry—Estimating the Maximum Safe Starting Dose in Initial Clinical Trials for Therapeutics . . . " US Department of Health and Human Services 2005.
Chen and Guillemin (2009) "Kynurenine Pathway Metabolites in Humans: Disease and Healthy States" Int. J. Tryptophan Res. 2:1-19.
Chen and Guillemin (Jan. 20, 2012) "The Kynurenine pathway" Chapter 15, Amyotrophic Lateral Sclerosis, book edited by Martin H. Maurer, ISBN 978-953-307-806-9.
Reagan-Shaw et al. (2007) "Dose translation from animal to human studies revisited" FASEB J. 22:659-661.
Stoy et al. (2005) "Tryptophan metabolism and oxidative stress in patients with Huntington's disease" J. Neurochem. 93(3):611-623.

\* cited by examiner

TREATMENT OF BDNF-RELATED DISORDERS USING LAQUINIMOD

This application claims the benefit of U.S. Provisional Application No. 61/273,920, filed Aug. 10, 2009, the entire content of which is hereby incorporated by reference herein.

Throughout this application various publications are referenced. The disclosures of these publications in their entireties are hereby incorporated by reference into this application in order to more fully describe the state of the art to which this invention pertains.

BACKGROUND

Neurotrophic factors have a profound influence on developmental events such as naturally occurring cell death, differentiation and process outgrowth (Snider, 1989). The brain-derived neurotrophic factor (BDNF) is a neurotrophic factor which belongs to the neurotrophin family of growth factors. BDNF acts on certain neurons of the central nervous system (CNS) and the peripheral nervous system (PNS), helping to support the survival of existing neurons and encourage the growth and differentiation of new neurons and synapses (Acheson, 1995; Huang, 2001). Increasing BDNF has been associated with the treatment of a number of disorders including Parkinson's disease, Huntington's disease (HD), amyotrophic lateral sclerosis (ALS), depressive disorders, retinitis pigmentosa, erectile dysfunction, memory disorders, Rett syndrome; Alzheimer's Disease, bipolar disorder and acute mania.

Parkinson's disease is a chronic and progressive degenerative disease of the brain that impairs motor control, speech, and other functions. One of the most striking features of Parkinson's disease is that it primarily affects a restricted neuronal population in the brain. Although other neurons are also affected, the dopaminergic neurons of the substantia nigra pars compacta are the most vulnerable to the disease process (Chesselet, 2003). BDNF has potent effects on survival and morphology of mesencephalic dopaminergic neurons, increasing their survival, and thus its loss could contribute to death of these cells in Parkinson's disease (PD) (Hyman, 1991; Howell, 2000).

Huntington's disease (HD) is a neurodegenerative disorder characterized by motor, cognitive, and psychiatric symptoms and by a progressive degeneration of neurons in basal ganglia in brain cortex. Patients suffering from HD have significantly lower BDNF levels in serum compared to healthy controls (Ciammola, 2007).

Amyotrophic lateral sclerosis (ALS) is a chronic and debilitating neurodegenerative disease which involves degeneration of cortical, bulbar and medullar motor neurons. Riluzole (2-amino-6-[trifluoromethoxy]benzothiazole) is an antagonist of glutamatergic neurotransmission that prolongs survival in ALS (Riviere, 1998). Riluzole has also been shown to significantly increase BDNF levels in the rat brain, thereby promoting precursor proliferation (Katoh-Semba, 2002).

Depression is another indication in which BDNF has been shown to have an effect. In a meta-analysis which encompasses many studies, depressed patients were shown to have lower BDNF levels than healthy control subjects, and antidepressant therapy has been shown to increase BDNF levels in depressed patients after treatment (Sen, 2008).

Retinitis pigmentosa is a disease associated with retinal photoreceptor cell loss. It has been shown that BDNF culturing of retina explants from rd mice, who suffer from a mutation in the same gene that has been found mutated in human autosomal recessive retinitis pigmentosa, showed an increase in number of photoreceptor nuclei in the outer nuclear layer (Caffe Romeo, 2001). This suggests that increasing BDNF levels in humans suffering from retinitis pigmentosa may slow the progression of the disease.

Erectile dysfunction is another disease which has been shown to be associated with BDNF. In U.S. Pat. No. 7,485,311, example 3, it was shown that treatment of rats in the bilateral cavernous nerve freezing model using intracavernous injection of AAV-BDNF improves maximum intracavernous pressure in response to bilateral cavernous nerve electrostimulation.

BDNF has also been associated with learning and memory. In a transgenic mouse model of BNF knockout mice, impairment of BDNF production has been shown to cause impairments in learning and memory in the adult stage and especially during early development (Monteggia, 2007). In a rat model, it was shown that endogenous BDNF in the hippocampus is involved in memory formation. Whereas infusion of function-blocking anti-BDNF antibody was shown to impair short term and long term memory in a model of fear-motivated learning, infusion of recombinant human BDNF facilitated long-term memory retention (Alonsa, 2005). Increasing BDNF levels in human patients in need of learning or memory improvement may also improve short and long term memory.

Rett Syndrome (RTT) is an X-linked neurodevelopmental disorder and the leading cause of severe mental retardation in females, affecting 1:10,000-15,000 births worldwide (Amaral, 2007). The disease is associated with mutations in the gene MeCP2. One of the targets of MeCP2 is the BDNF gene. This suggests that deregulation of BDNF expression in Rett Syndrome may be the cause of structural anomalies observed in patients, especially the reduced dendritic branching and loss of dendritic spines (Amaral, 2007). This suggests that increasing BDNF levels in Rett syndrome may be a viable therapy in treating the disease.

In bipolar disorder patients suffering from acute mania, levels of BDNF were shown to vary depending upon whether the patient was treated or untreated. Before treatment with known mania treatments, BDNF levels were found to be lower than in healthy controls, but upon treatment, the difference between BDNF levels in serum of treated patients and controls was no longer significant (Tramontina, 2009). It may be possible to treat acute mania by increasing BDNF levels in patients in need thereof.

Several agents have been identified to increase BDNF levels including riluzole and antidepressants such as fluoxetine (Prozac®) (Katoh-Semba, 2002; Molteni, 2006).

SUMMARY OF THE INVENTION

Disclosed herein is another agent, i.e., Laquinimod, which has been shown to increase BDNF in humans. Laquinimod is a novel synthetic compound with high oral bioavailability, which has been suggested as an oral formulation for Relapsing Remitting Multiple Sclerosis (RRMS). The relationship between laquinimod and BDNF has not been reported. Laquinimod is a compound whose chemical name is N-ethyl-N-phenyl-1,2-dihydro-4-hydroxy-5-chloro-1-methyl-2-oxoquinoline-3-carboxamide, and its Chemical Registry number is 248281-82-7. The process of synthesis of laquinimod and the preparation of its sodium salt are disclosed in U.S. Pat. No. 6,077,851. Additional process of synthesis of laquinimod is disclosed in U.S. Pat. No. 6,875,869 and in U.S. Patent Application Publication No. 2007-0088050. Pharmaceutical compositions comprising laquinimod sodium are disclosed in PCT International Application Publication No. WO 2005/074899 as well as in U.S. Patent Application Publication Nos. 2007-0293537 and 2009-0162432.

This application provides for a method of increasing brain-derived neurotrophic factor (BDNF) serum level in a human subject comprising periodically administering to the subject an amount of laquinimod or pharmaceutically acceptable salt thereof effective to increase BDNF serum level in the human subject. The method can further comprise periodically administering to the subject an amount of a second BDNF-increasing agent.

This application also provides for a method for treating a human subject suffering from a BDNF-related disease selected from the group consisting of Parkinson's disease, Huntington's disease, amyotrophic lateral sclerosis, depressive disorders, anxiety disorders, retinitis pigmentosa, erectile dysfunction, memory disorders, Rett syndrome, Alzheimer's disease, bipolar disorder and acute mania comprising periodically administering laquinimod or a pharmaceutically acceptable salt thereof in an amount effective to treat the human subject.

This application also provides for use of laquinimod in the manufacture of a medicament for increasing BDNF serum level in a human subject.

This application also provides for a pharmaceutical composition comprising an amount of laquinimod effective for use in increasing BDNF serum level in a human subject.

This application also provides for a pharmaceutical preparation comprising an amount of laquinimod and an amount of a second BDNF-increasing agent effective for use in increasing BDNF serum level in a human subject.

4A: Effect of Laquinimod (1; 5; 10; 25 mg/kg/dx4,p.o., −90) and Fluoxetine (10 mg/kg/dx4, −90 min, p.o.) in the FST on Distance moved [cm] on Balb C mice [4 min]

4B: Effect of Laquinimod (1; 5; 10; 25 mg/kg/dx4, p.o., −90) and Fluoxetine (10 mg/kg/dx4, −90 min, p.o.) in the FST on Velocity (cm/s) on Balb C mice [4 min]

4C: Effect of Laquinimod (1; 5; 10; 25 mg/kg/dx4, p.o., −90) and Fluoxetine (10 mg/kg/dx4, −90 min, p.o.) in the FST on Movement (Moving duration) on Balb C mice [4 min]

4D: Effect of Laquinimod (1; 5; 10; 25 mg/kg/dx4, p.o., −90) and Fluoxetine (10 mg/kg/dx4, −90 min, p.o.) in the FST on Immobility total duration [10%] on Balb C mice [4 min]

FIG. 5: Shows Forced Swim Test results conducted in Example 2.2. (*p<0.01 vs. cont) Laquinimod (0.5-25 mg/kg/dx3d po) showed antidepressant activity with doses at 5 and 25 mg/kg inducing significant antidepressant activity.

5A: Effect of Laquinimod (0.5; 1; 5; 25 mg/kg, p.o., −90) and Fluoxetine (10 mg/kg, −90 min, p.o.) in the FST on Distance moved [cm] on Balb C mice [4 min]

5B: Effect of Laquinimod (0.5; 1; 5; 25 mg/kg, p.o., −90) and Fluoxetine (10 mg/kg, −90 min, p.o.) in the FST on velocity Balb C mice [4 min]

5C: Effect of Laquinimod (0.5; 1; 5; 25 mg/kg, p.o., −90) and Fluoxetine (10 mg/kg, −90 min, p.o.) in the FST on movement (total duration) on Balb C mices [4 min]

5D: Effect of Laquinimod (0.5; 1; 5; 25 mg/kg, p.o., −90) and Fluoxetine (10 mg/kg, −90 min, p.o.) in the FST on Immobility total duration [10%] on Balb C mice [4 min]

FIG. 6: Shows Open Field Test—motility parameter results conducted in Example 3.1. (N=5/group) Laquinimod (1-25 mg/kg/dx3d po) did not modify general mobility parameters in open field in Balb/c mice.

6A: Effect of Laquinimod (1; 5; 10; 25 mg/kg, po; −90 min) and Fluoxetine (10 mg/kg, po; −90 min) and combination in the Open field test on Distance moved [cm] on BALB/c mice [20 min]

6B: Effect of Laquinimod (1; 5; 10; 25 mg/kg, po; −90 min) and Fluoxetine (10 mg/kg, po; −90 min) and combination in the Open field test on Velocity mean [cm/s] on BALB/c mice [20 min]

6C: Effect of Laquinimod (1; 5; 10; 25 mg/kg, po; −90 min) and Fluoxetine (10 mg/kg, po; −90 min) and combination in the Open field test on Immobility total duration on BALE/c mice [20 min]

6D: Effect of Laquinimod (1; 5; 10; 25 mg/kg, po; −90 min) and Fluoxetine (10 mg/kg, po; −90 min) and combination in the Open field test on Strong mobility total duration [s] on BALE/c mice [20 min]

FIG. 7: Shows Open Field Test—anxiety parameter results (in zone 2) conducted in Example 3.1. (N=5/group) Laquinimod (1-25 mg/kg/dx3d po) showed tendency toward anxiolytic effect with animals being more active in the center (zone 2).

Figure 1:
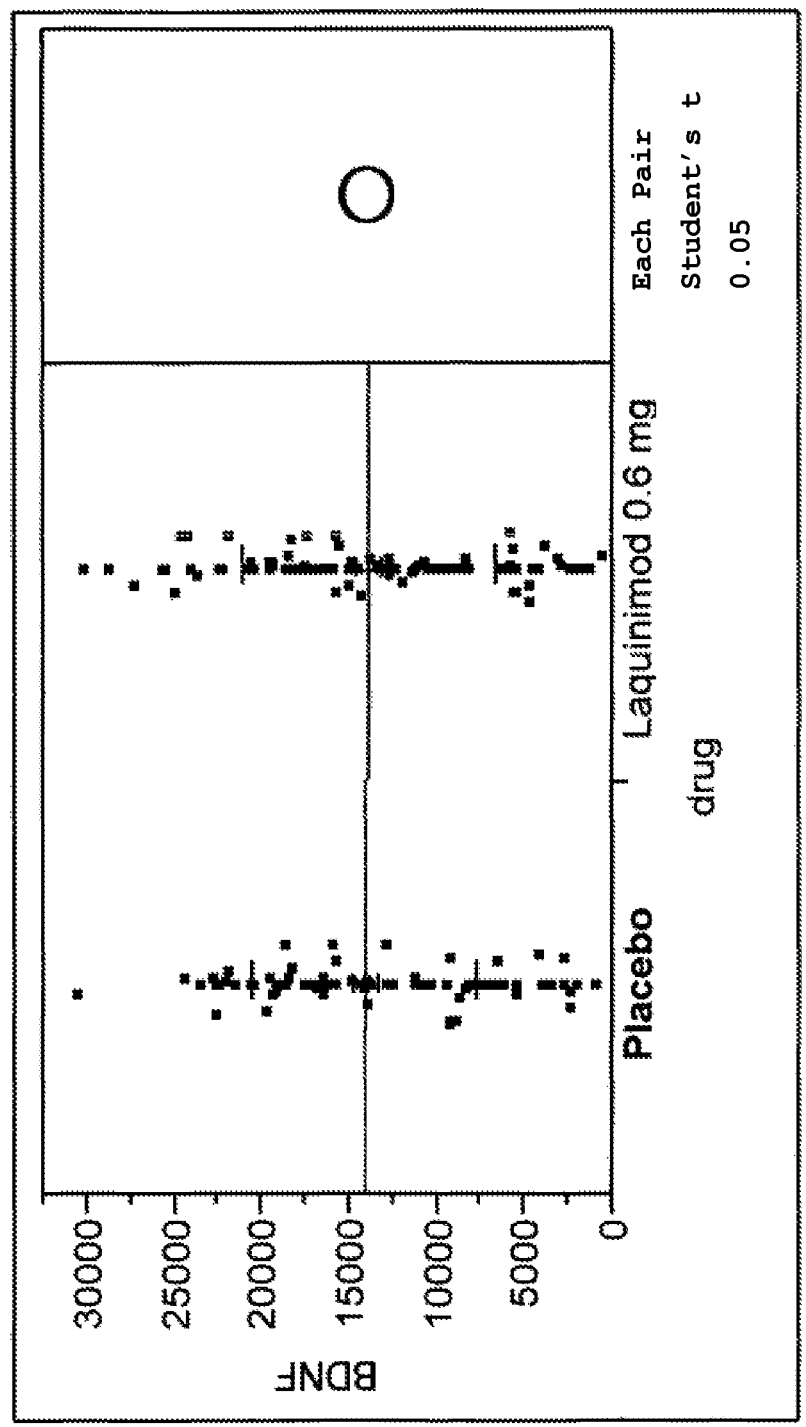
FIG. 1: Shows one-way analysis of BDNF comparing the placebo group and 0.6 mg laquinimod group at baseline.
Figure 2:
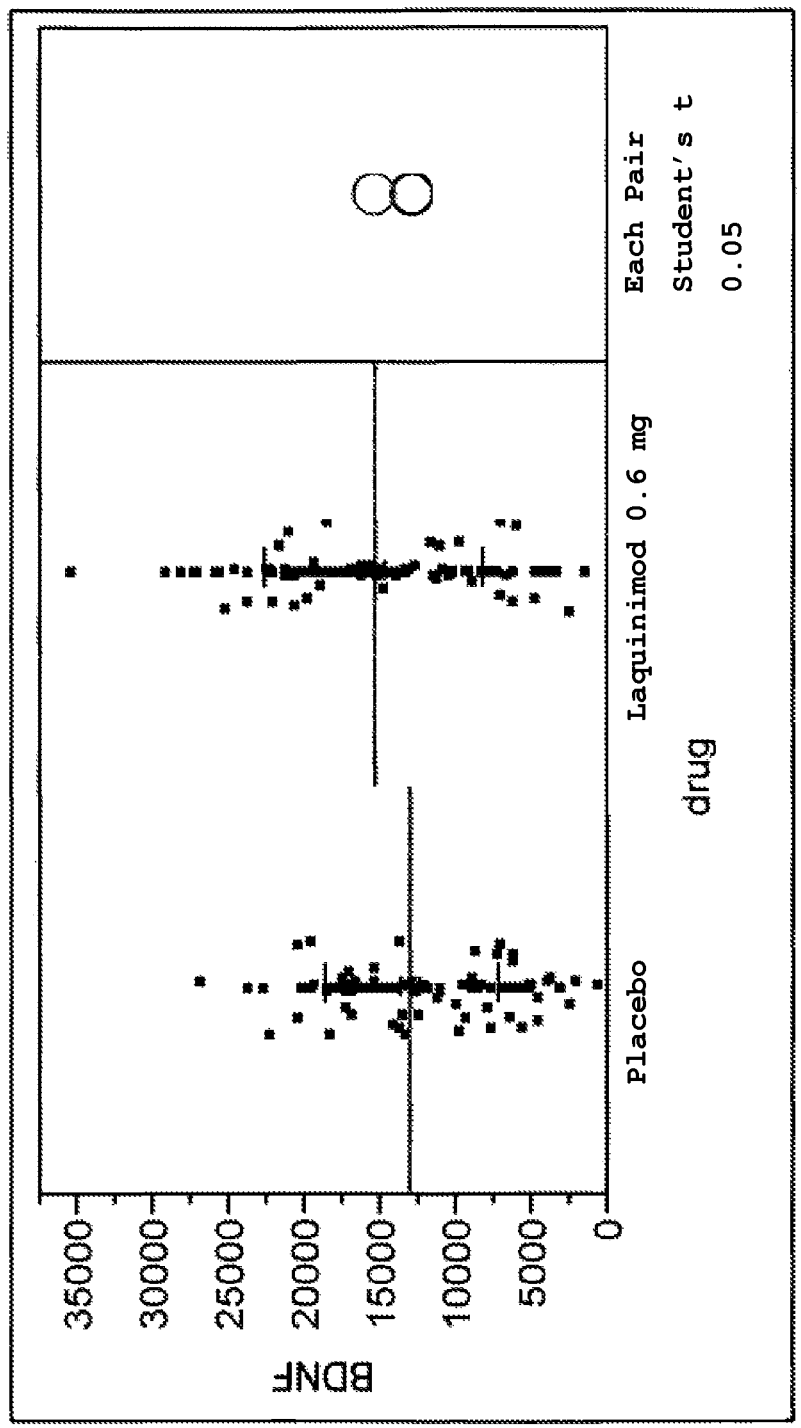
FIG. 2: Shows one-way analysis of BDNF comparing the placebo group and 0.6 mg laquinimod group at week 12 (V3).
Figure 3:
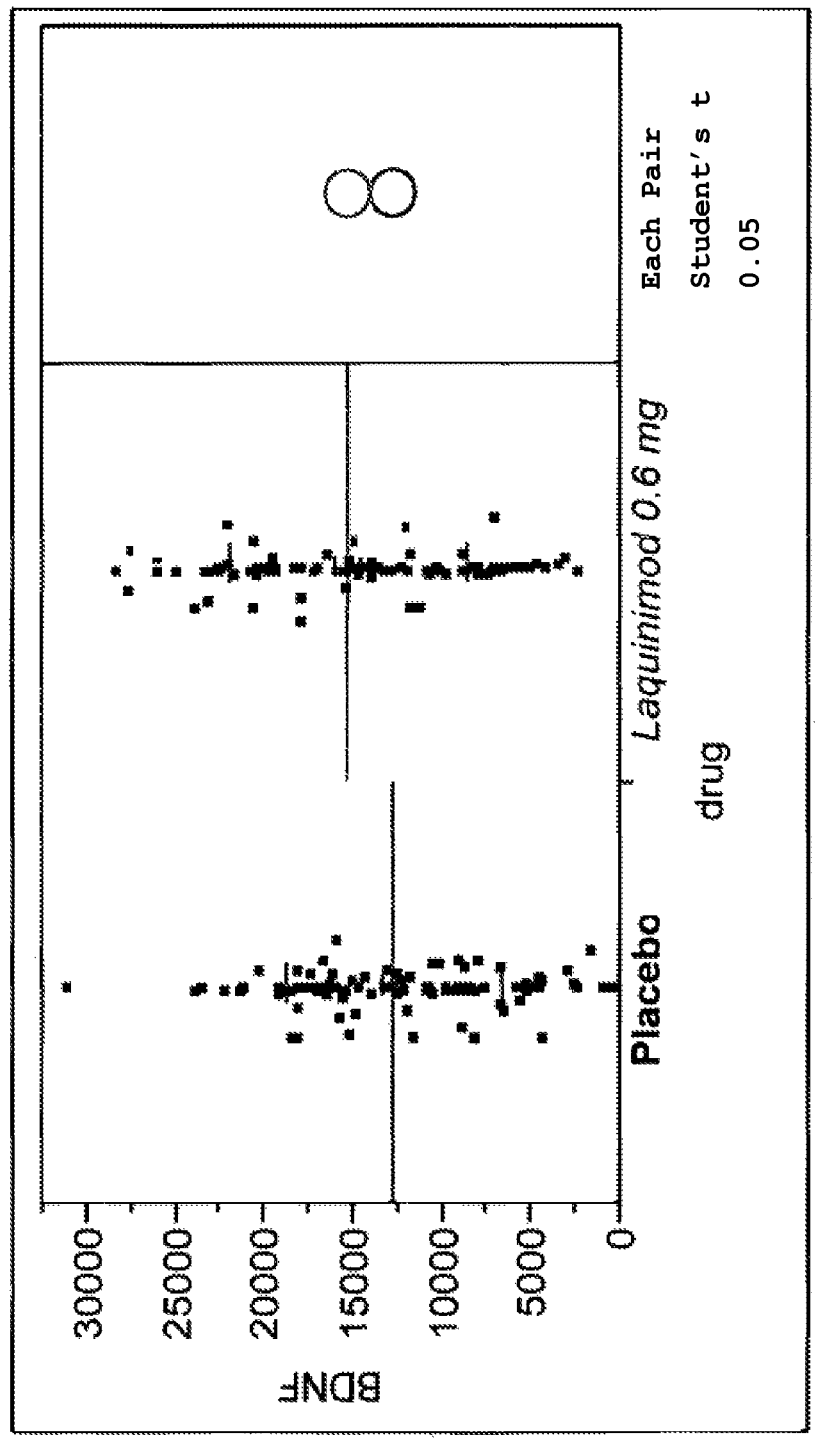
FIG. 3: Shows one-way analysis of BDNF comparing the placebo group and 0.6 mg laquinimod group at week 36 (V9).
Figure 4A:
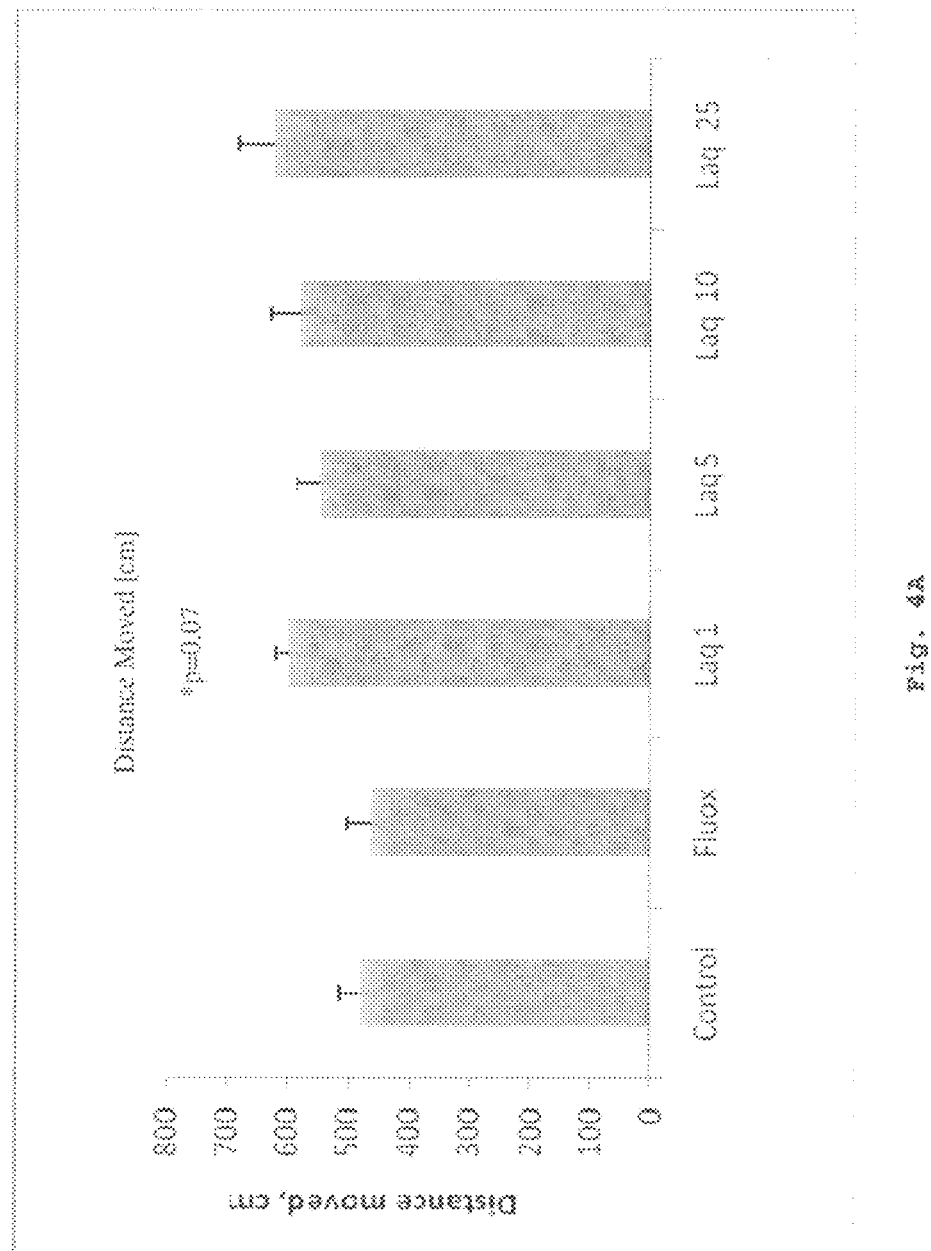
FIG. 4: Shows Forced Swim Test results conducted in Example 2.1. (N=5/group) Laquinimod (1-25 mg/kg/dx3d po) showed antidepressant activity with the 1 mg/kg p.o. dose being the most active.
Figure 4B:
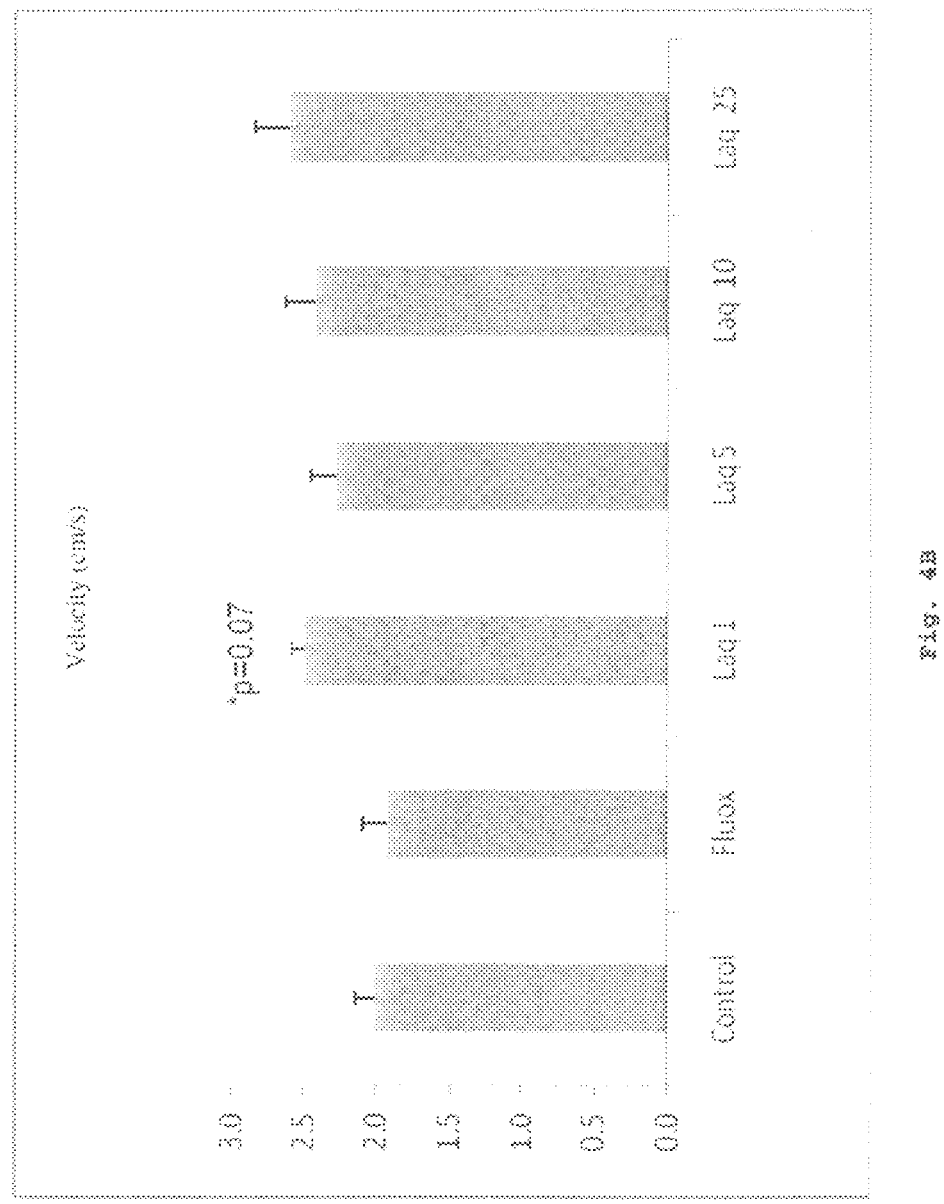
Figure 4C:
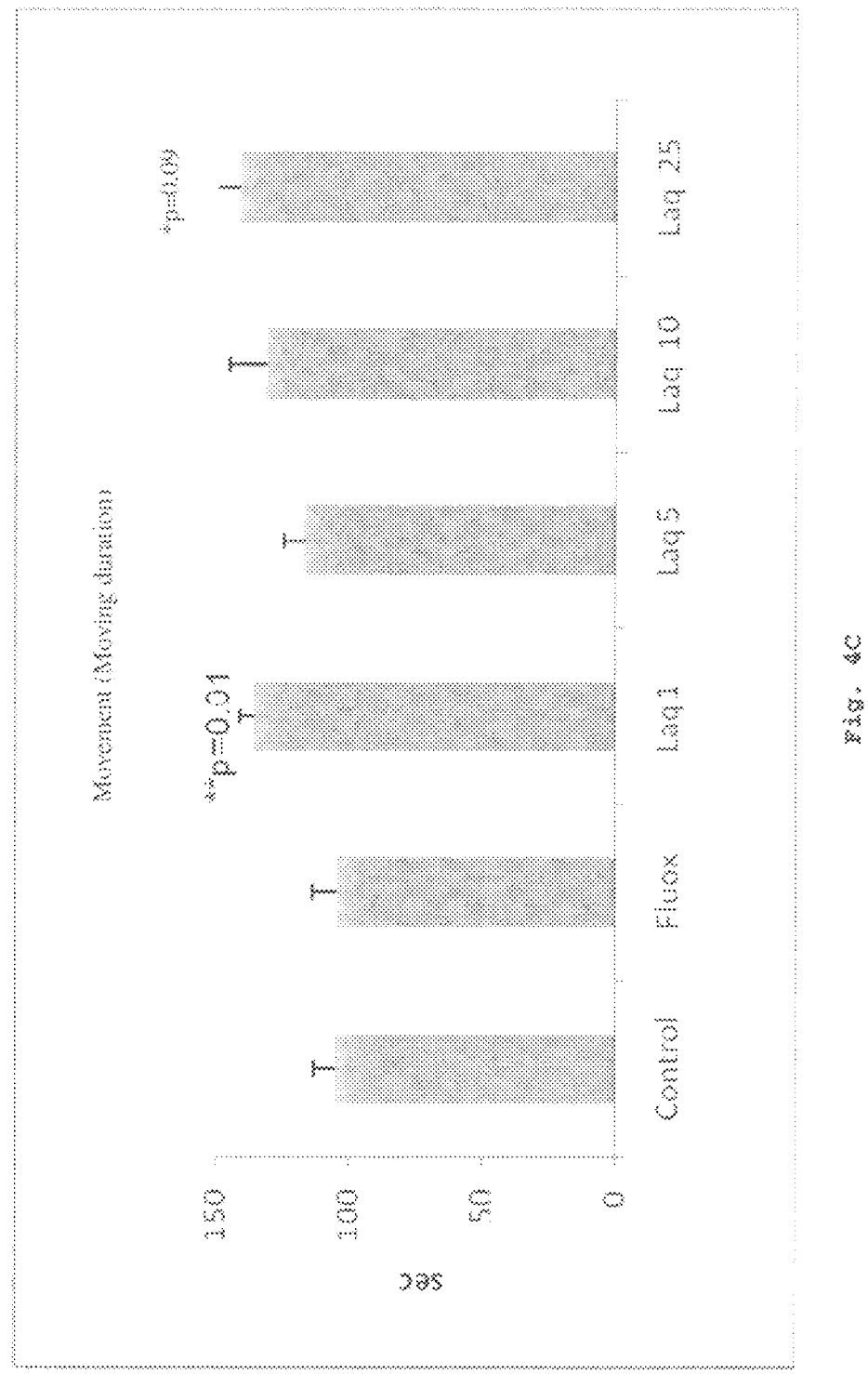
Figure 4D:
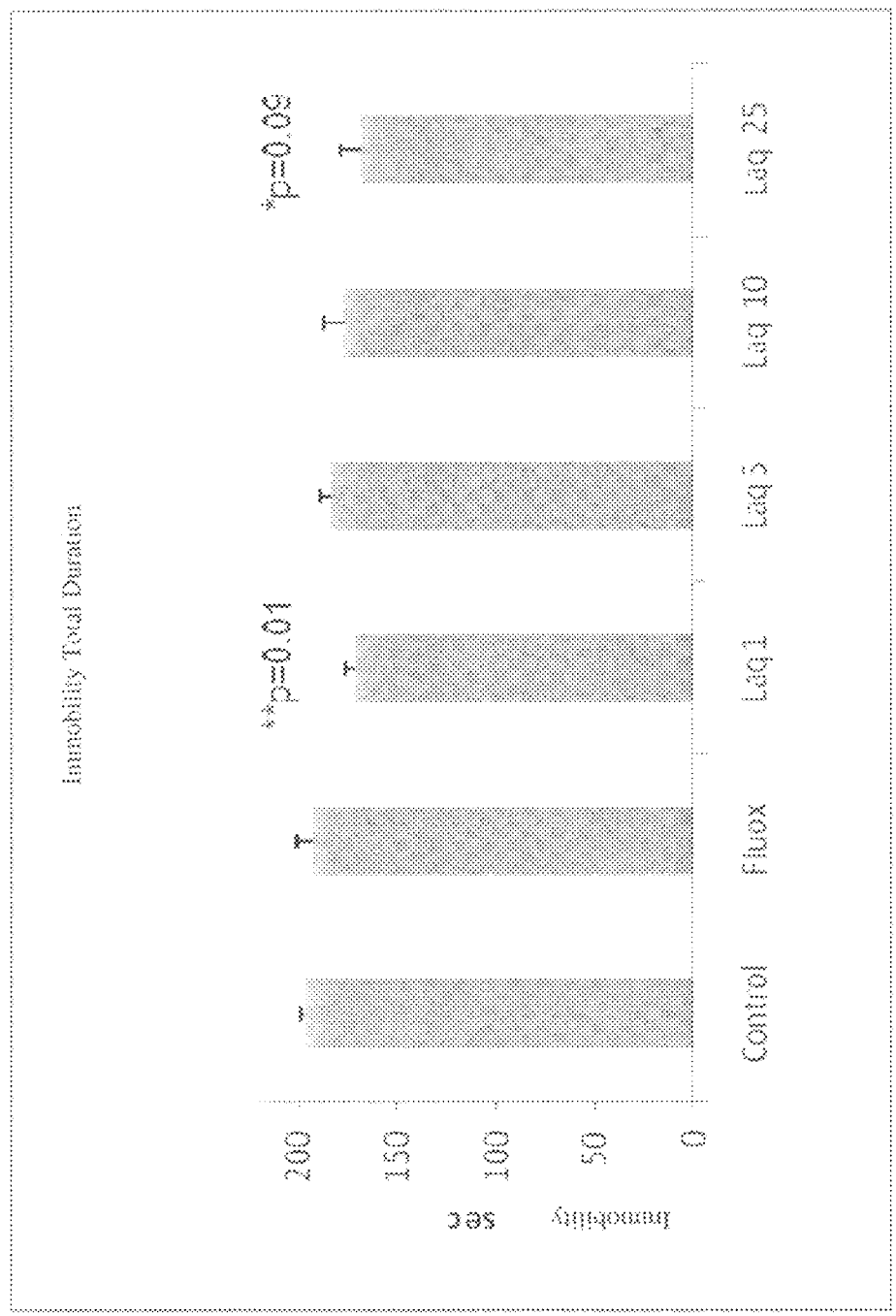
Figure 5A:
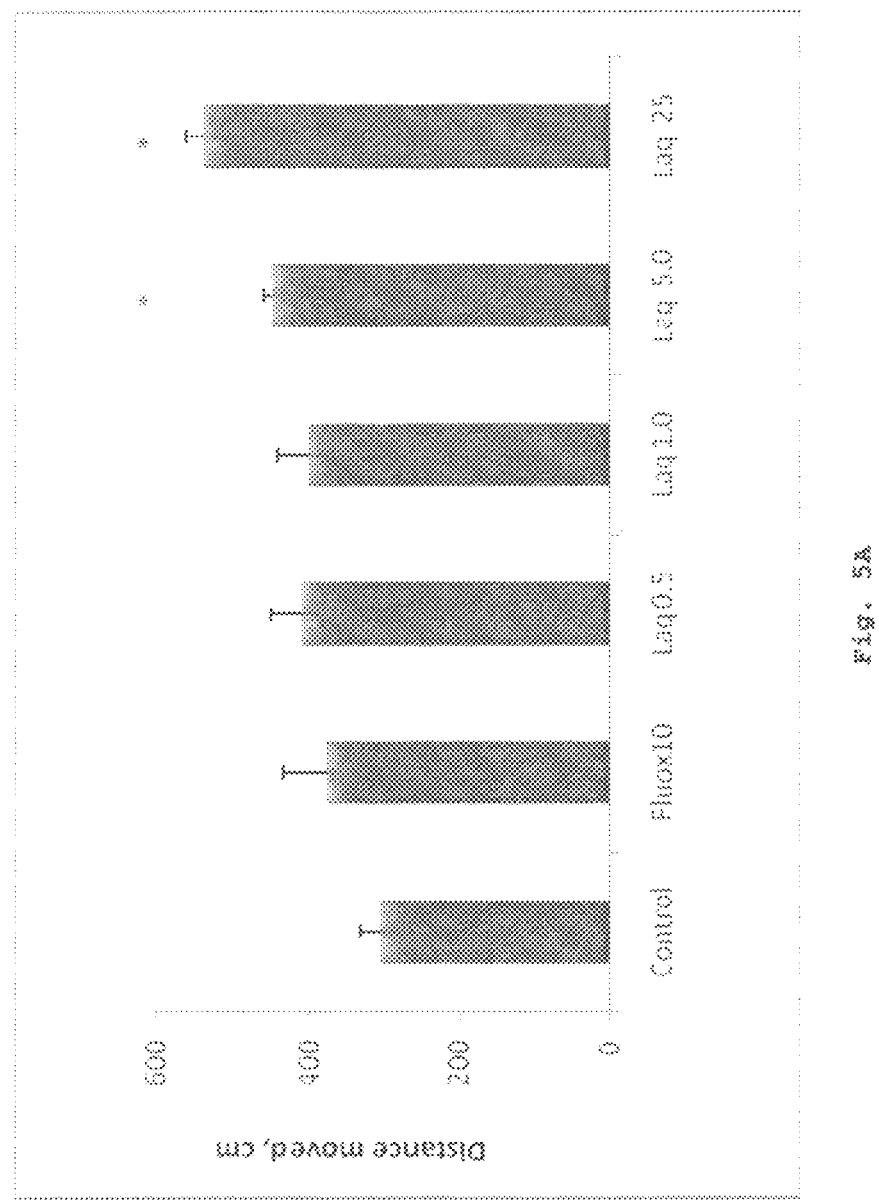
Figure 5B:
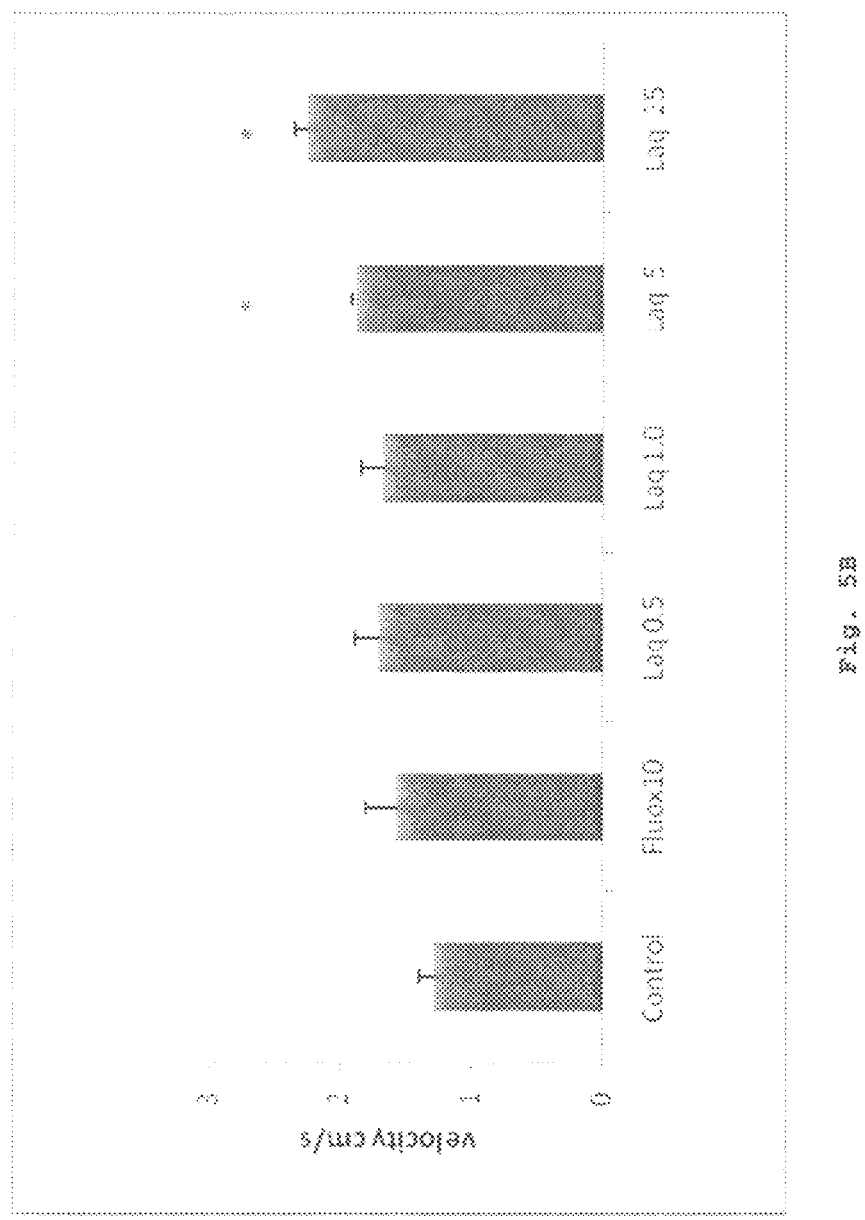
Figure 5C:
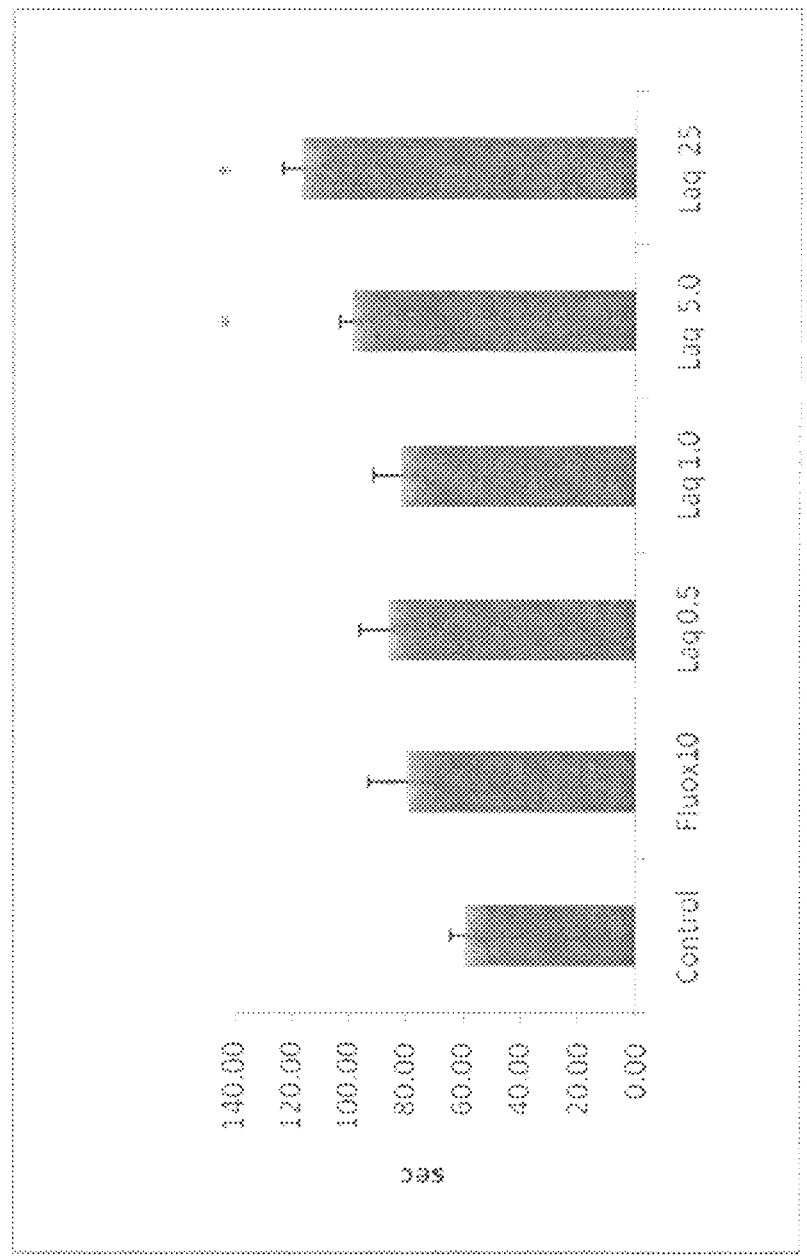
Figure 5D:
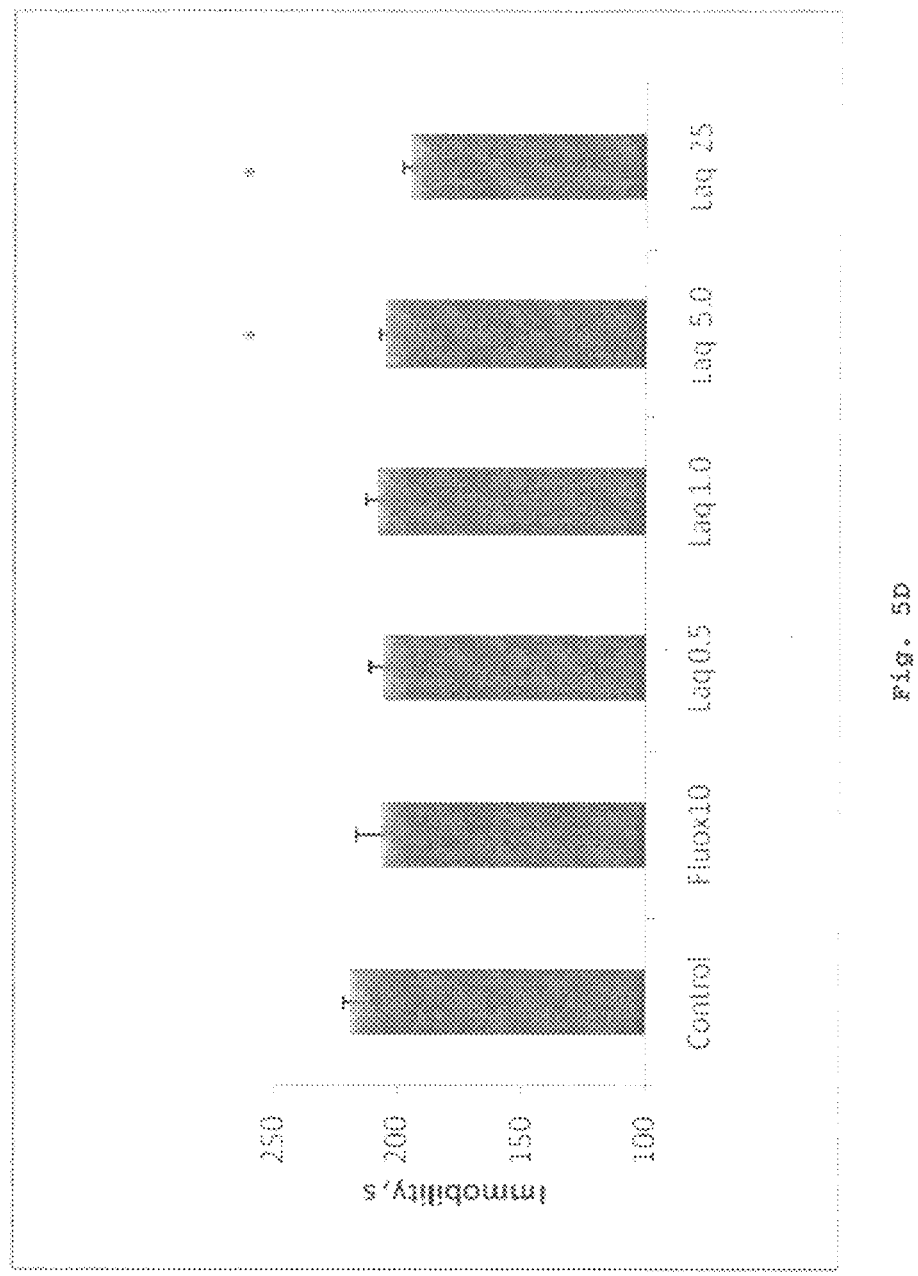
Figure 6A:
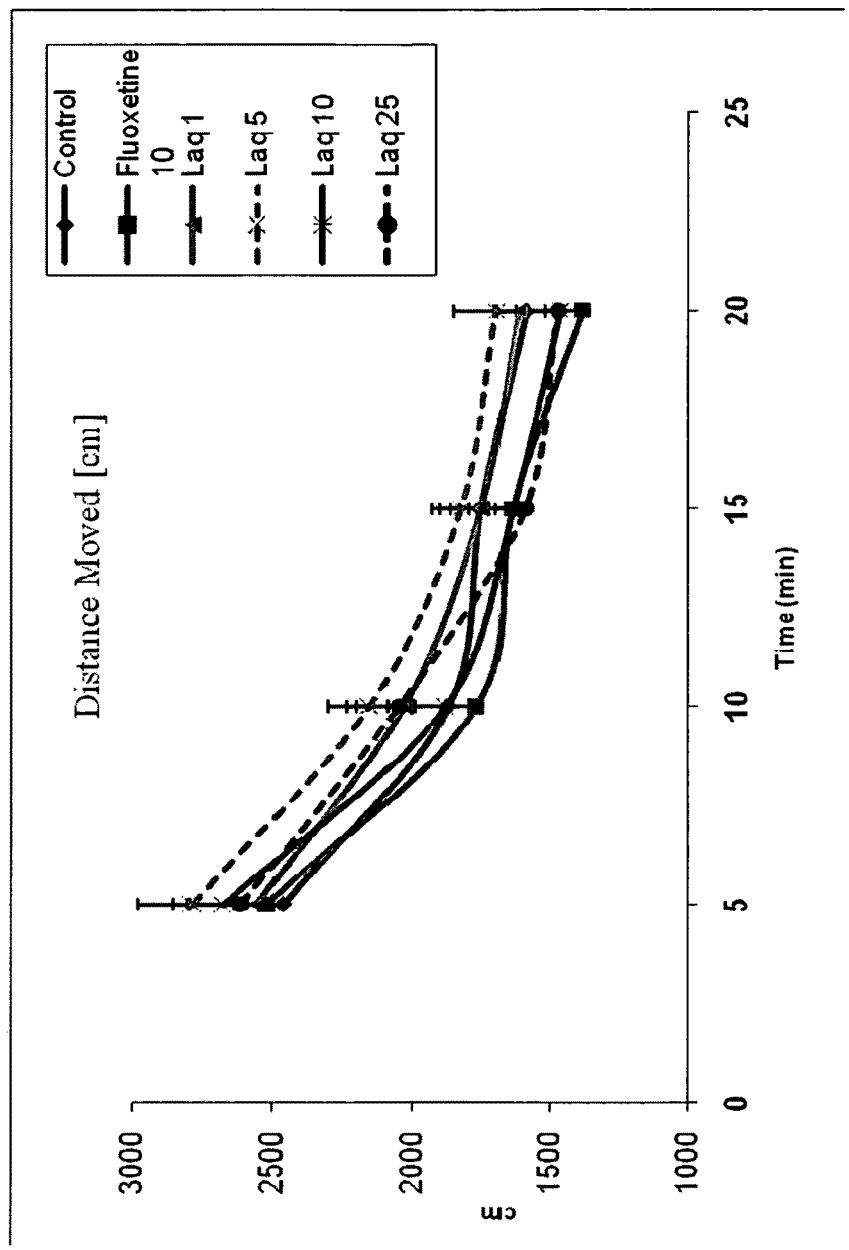
Figure 6B:
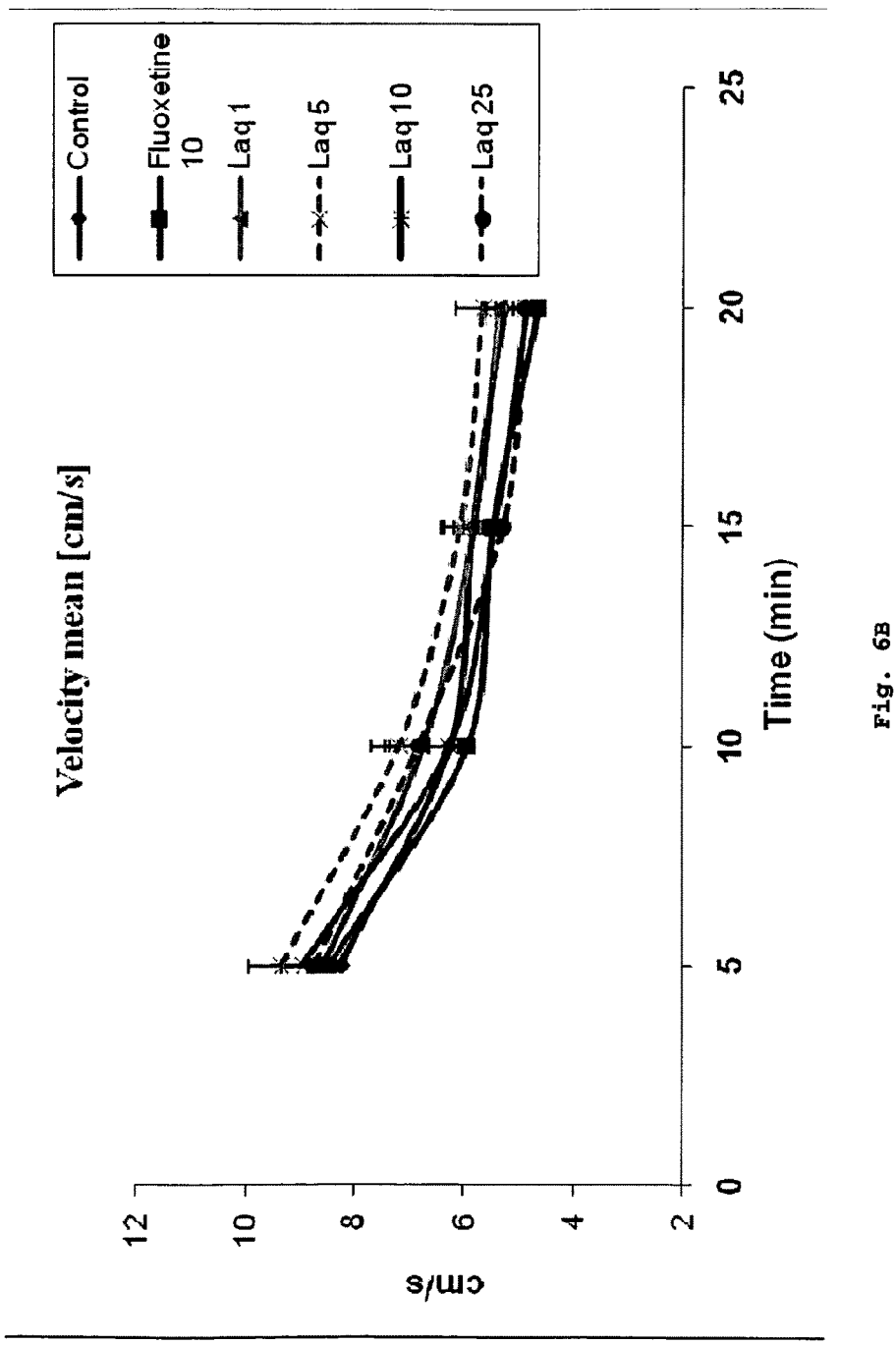
Figure 6C:
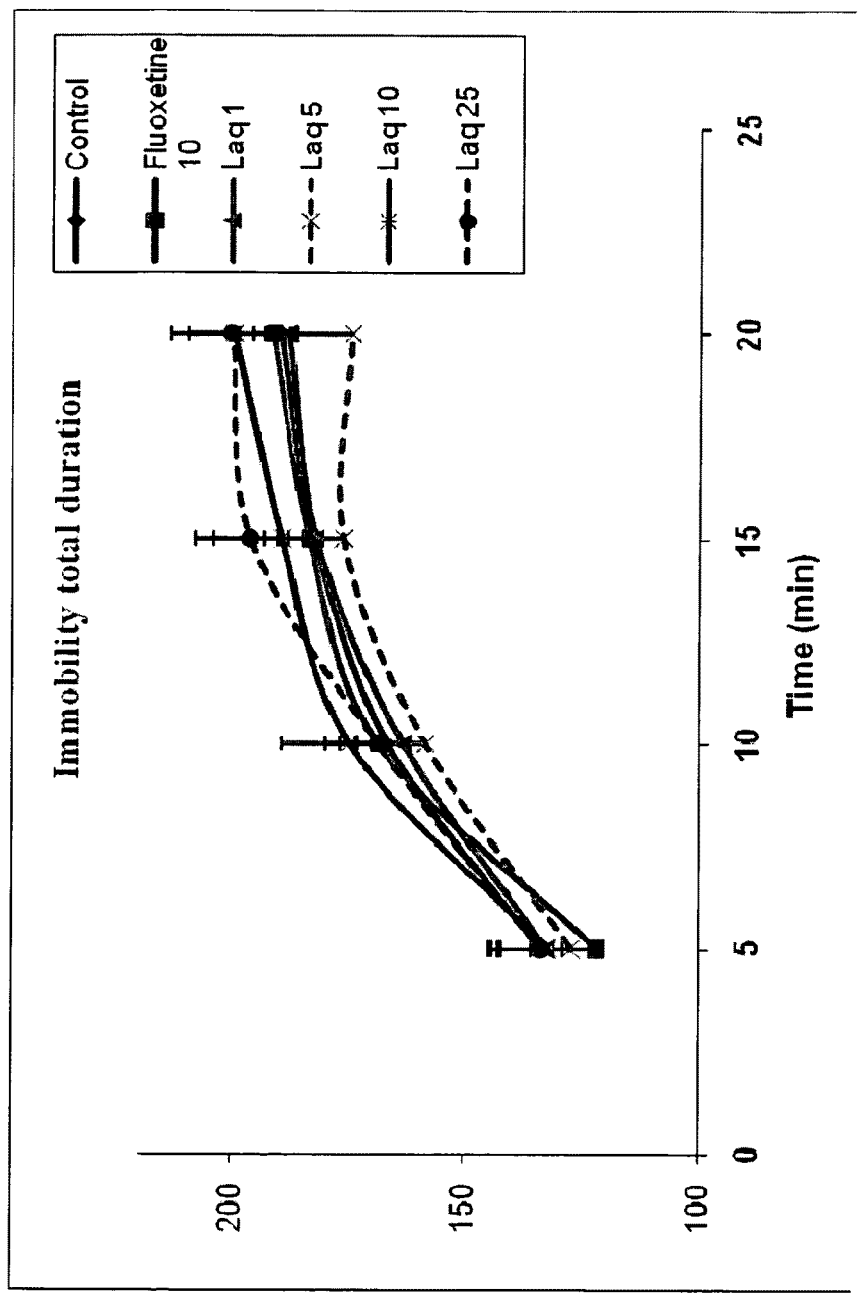
Figure 6D:
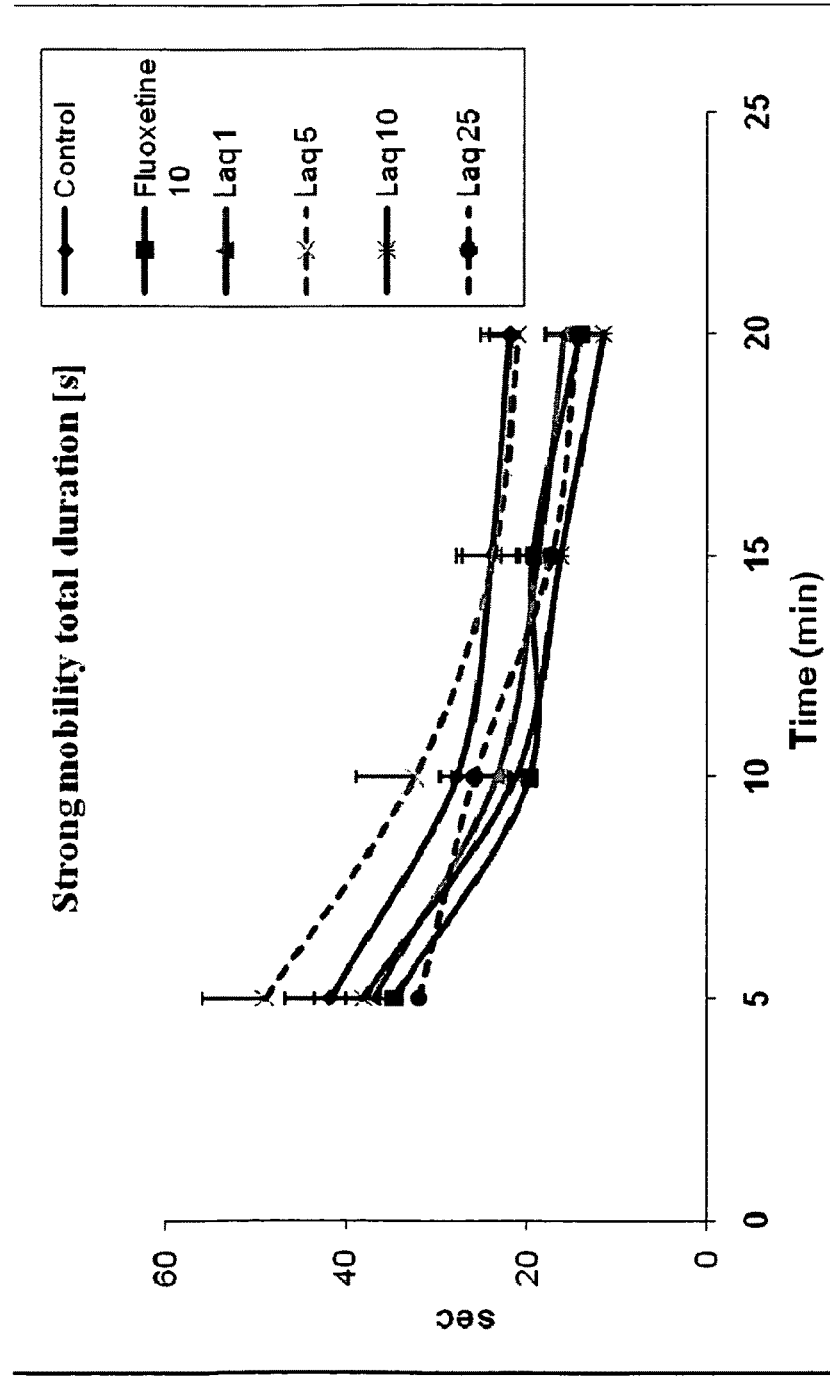
Figure 7A:
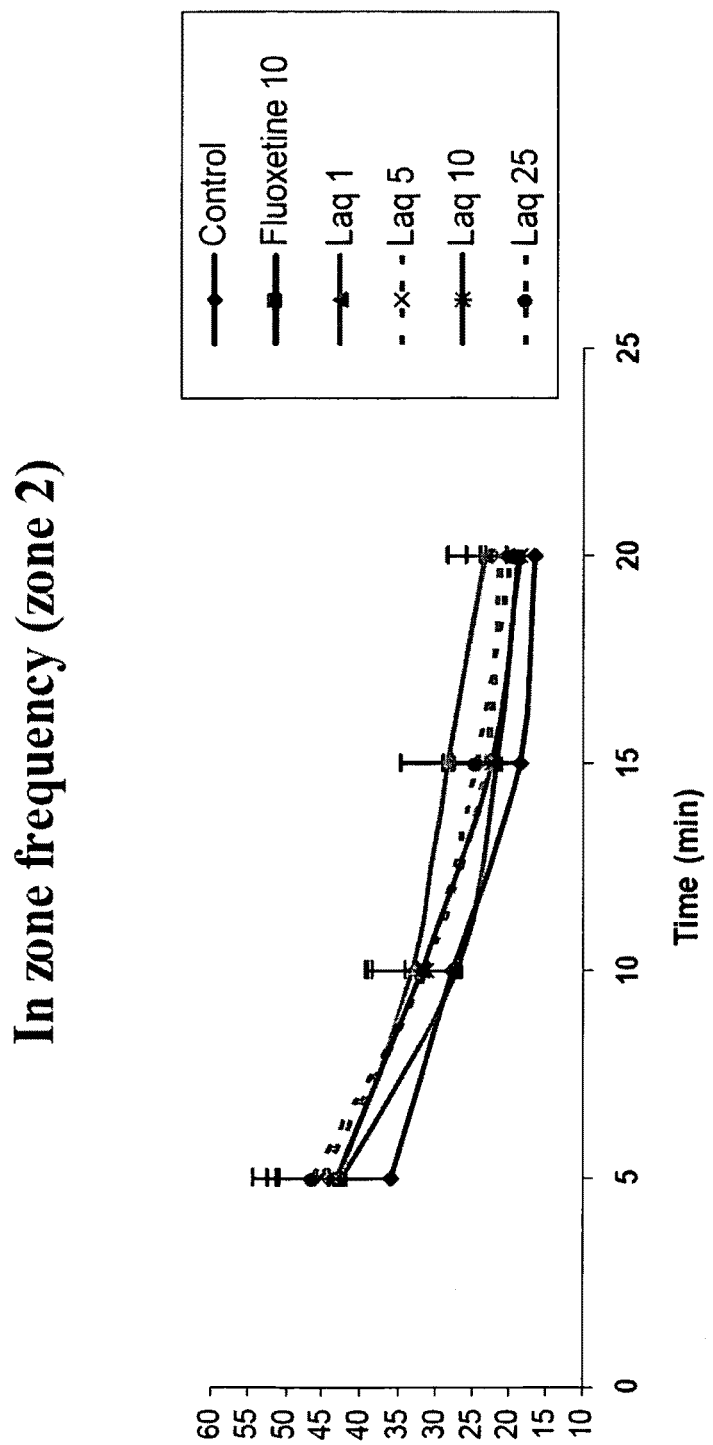
Figure 7B:
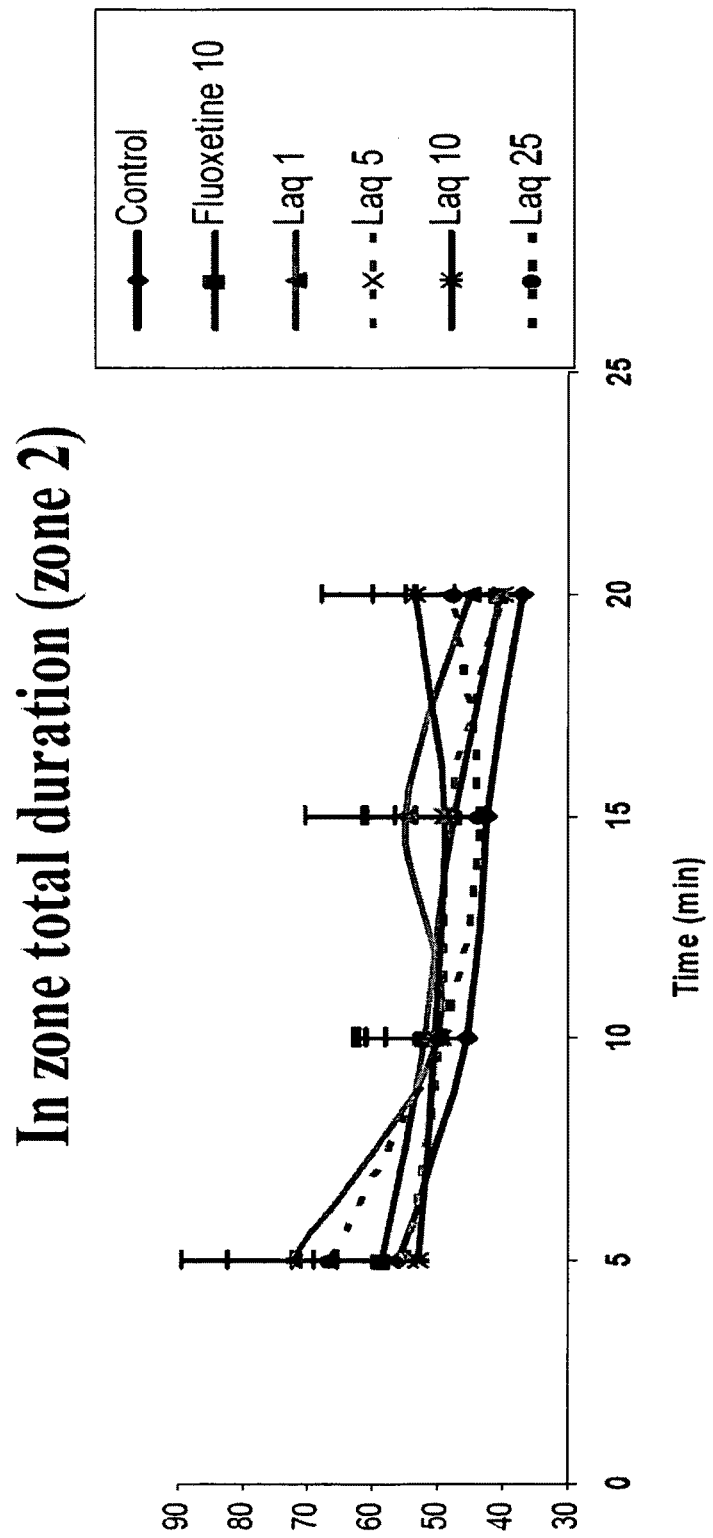
Figure 7C:
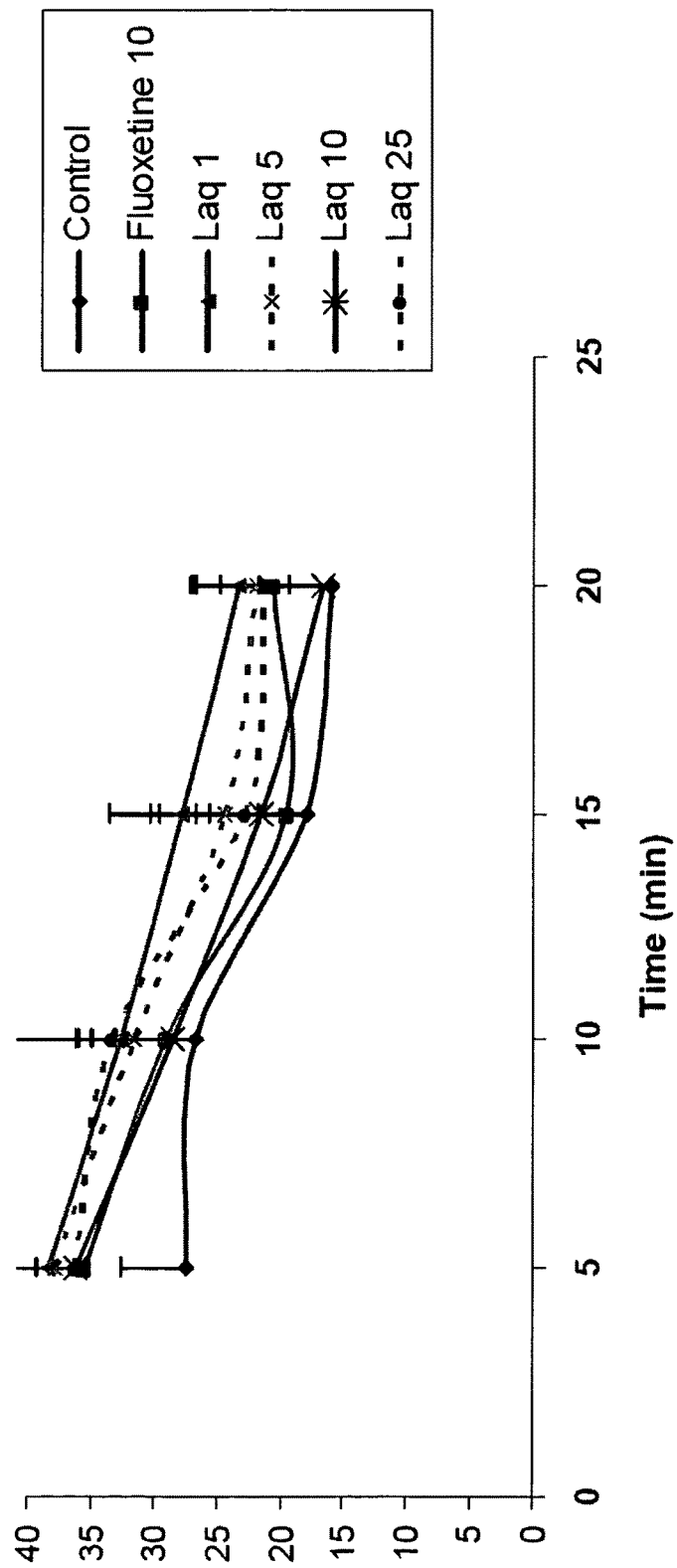
Figure 7D:
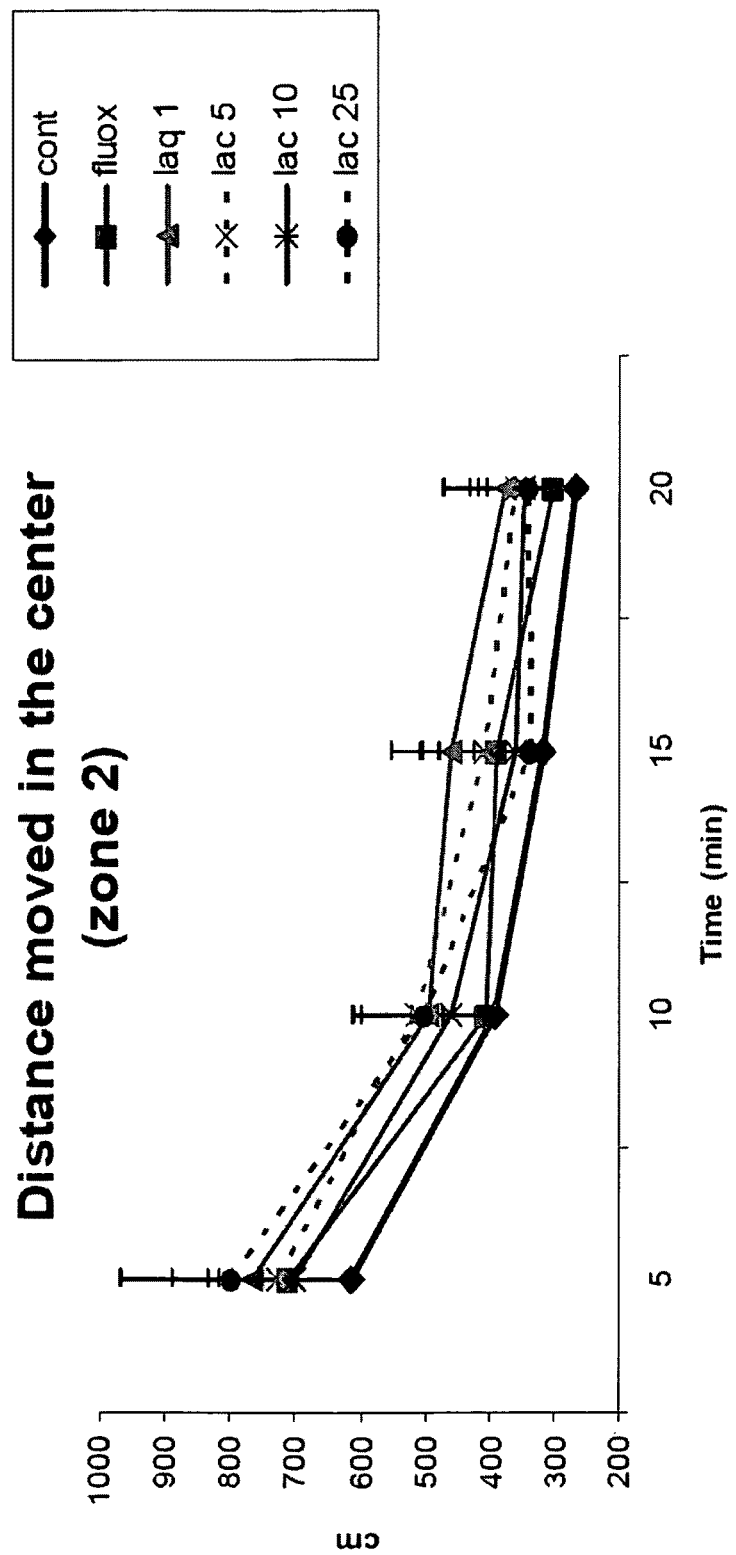
Figure 8A:
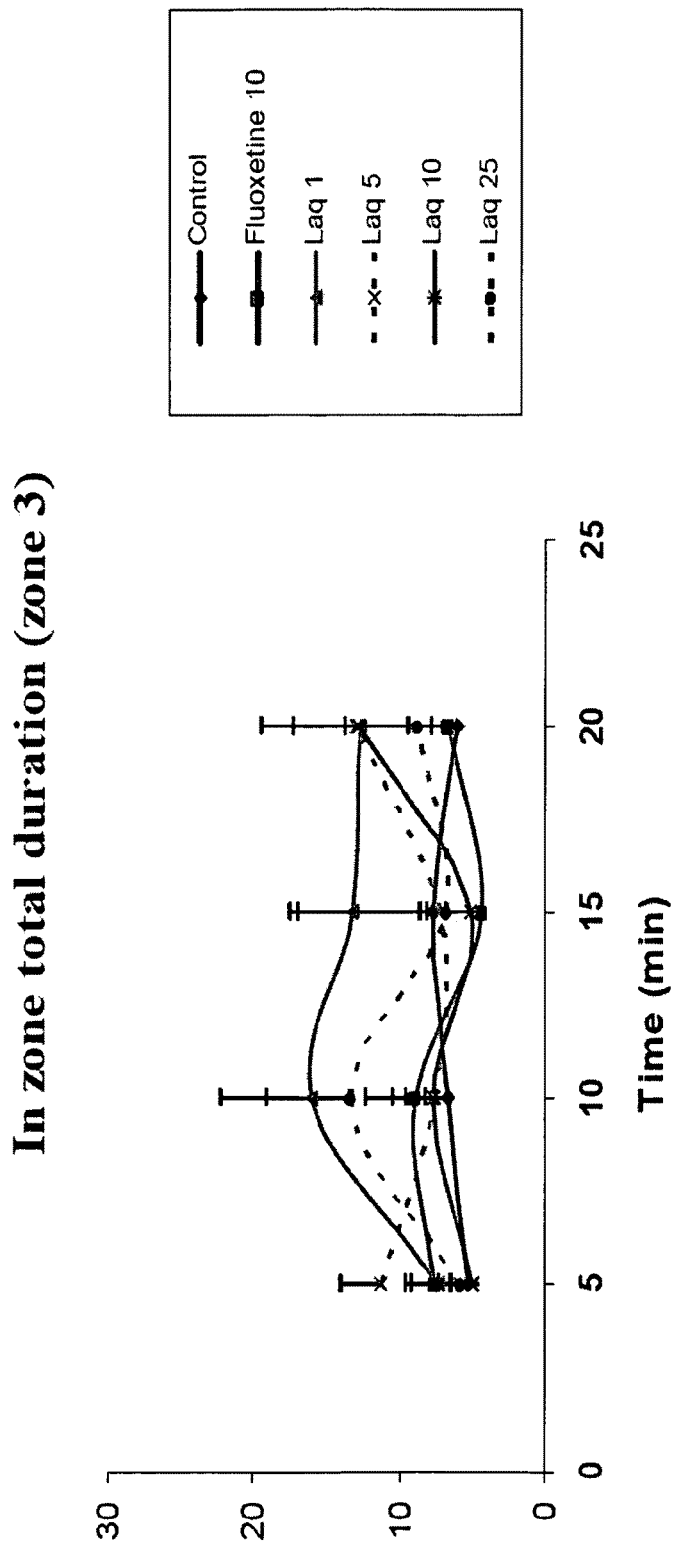
Figure 8B:
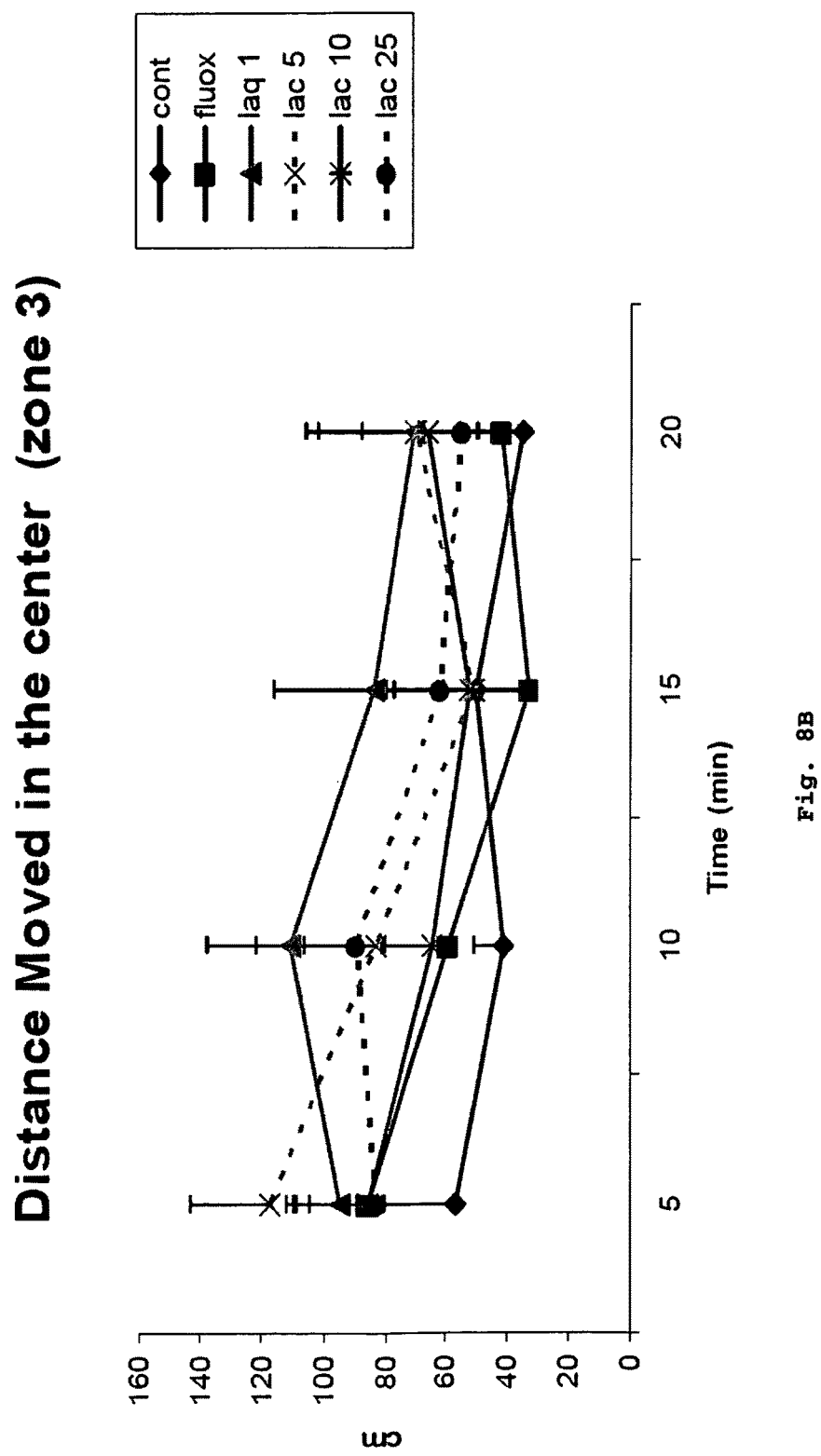
Figure 8C:
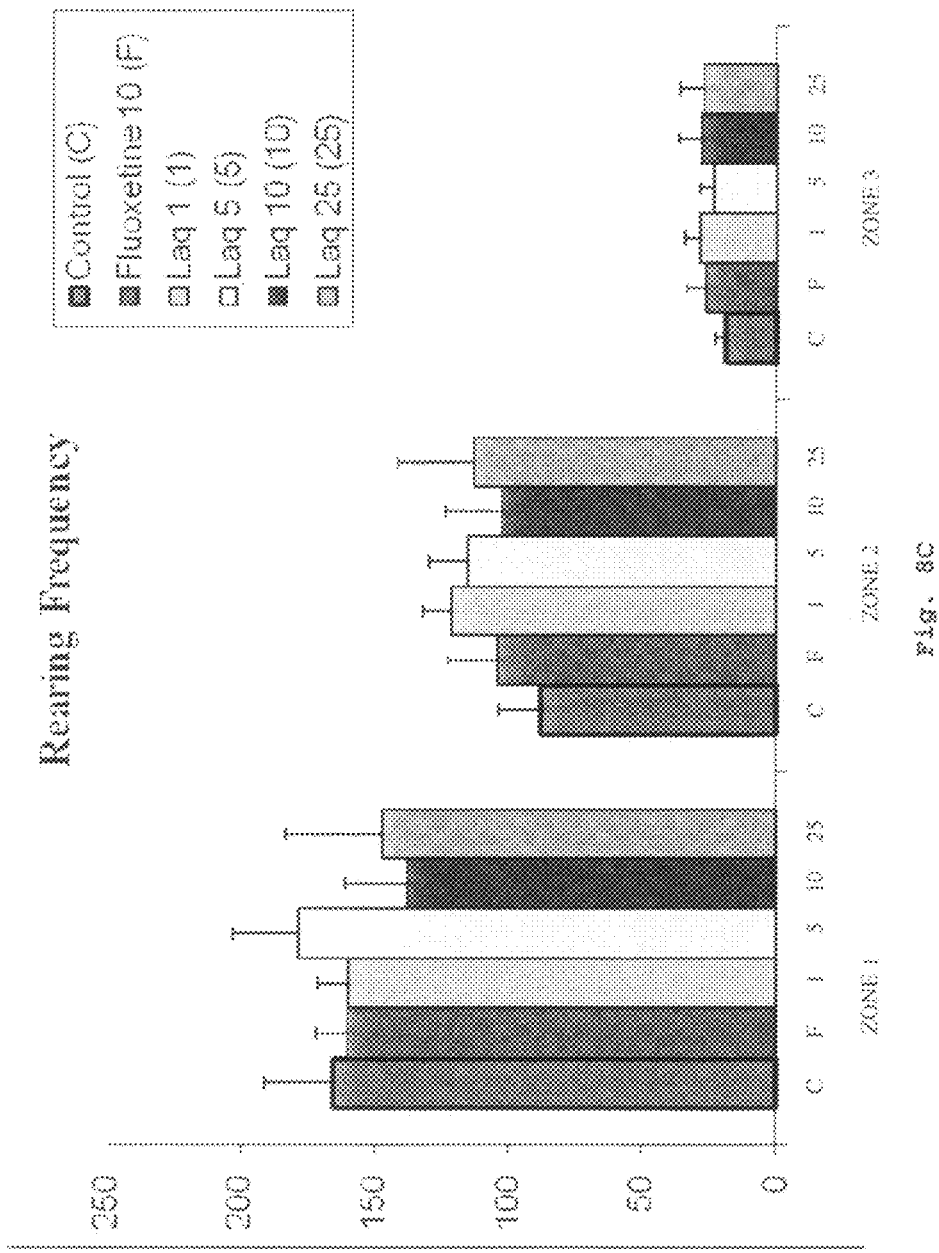
Figure 9A:
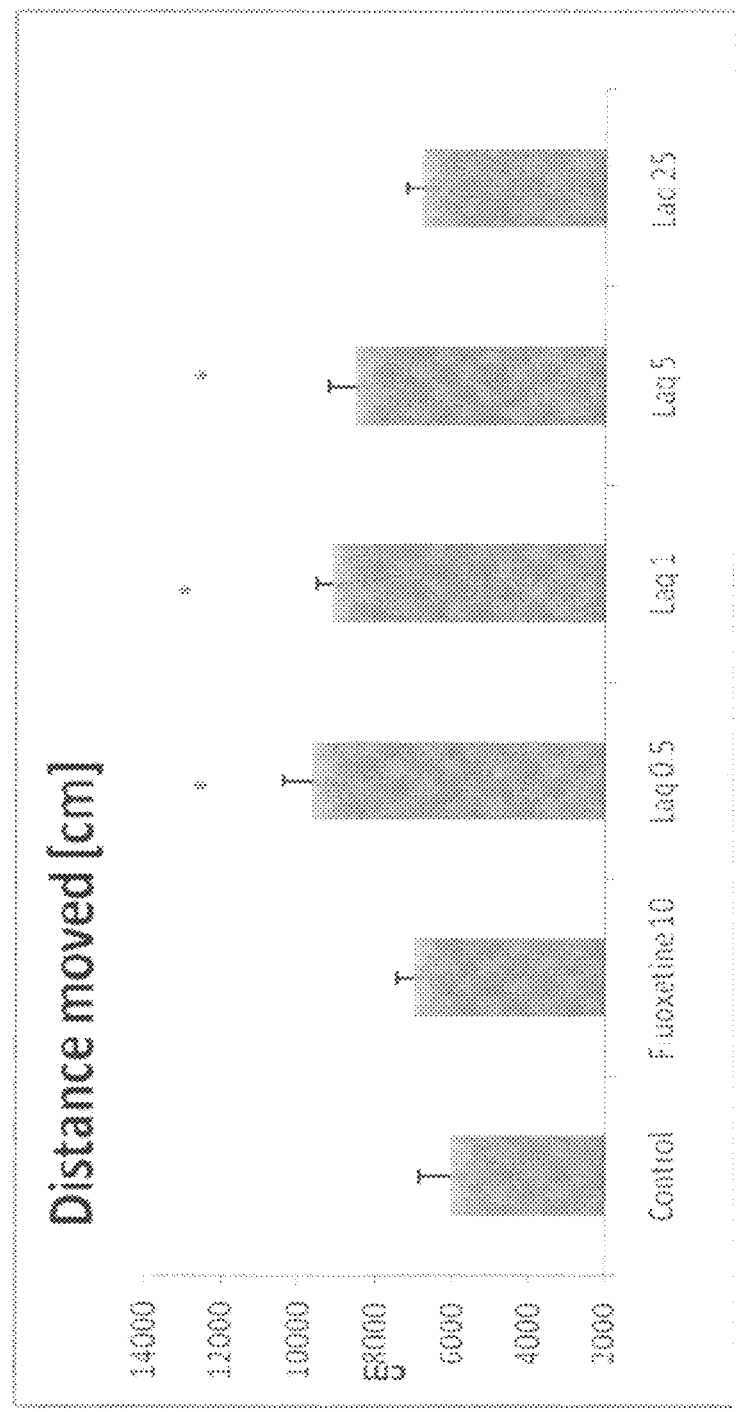
Figure 9B:
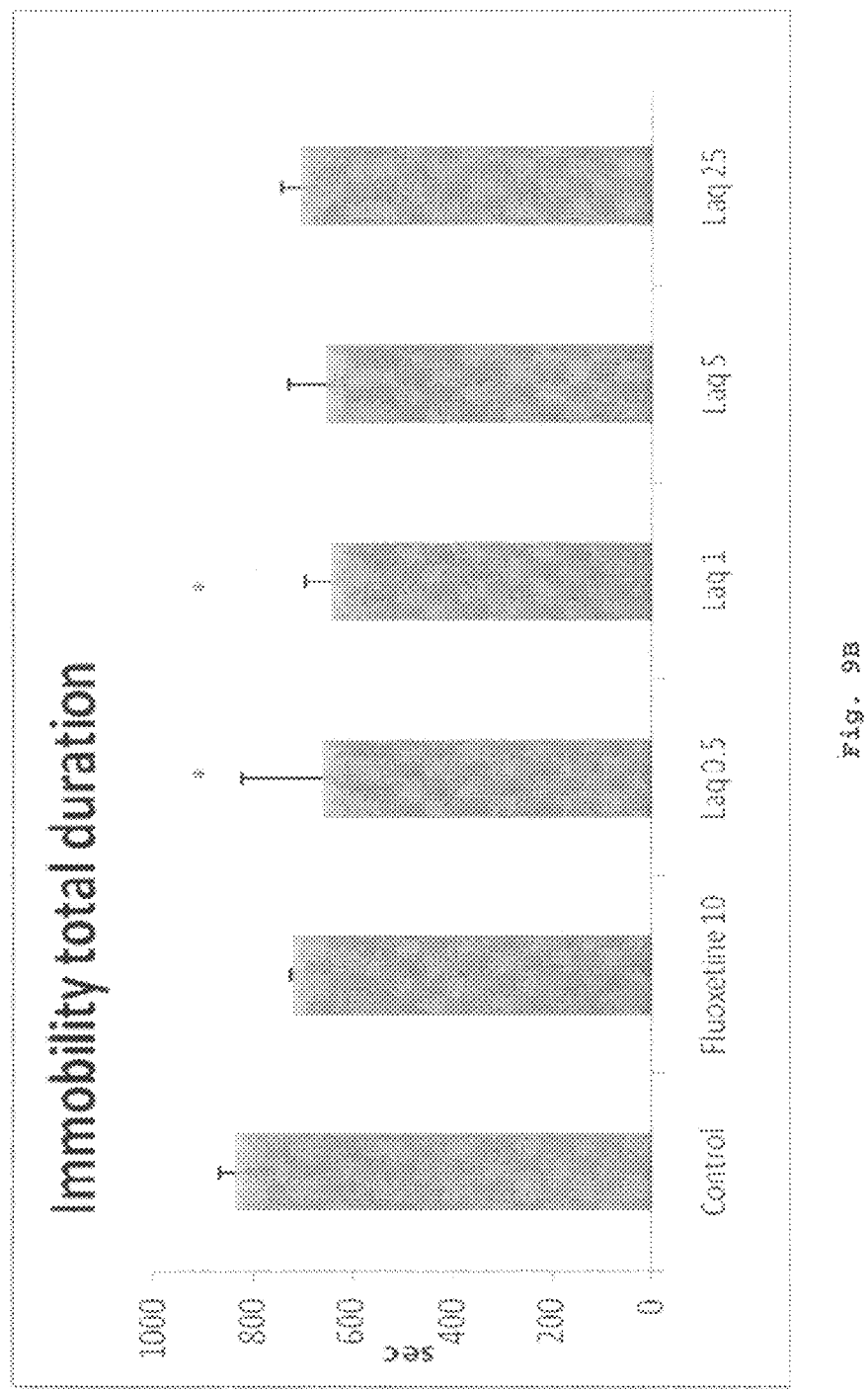
Figure 9C:
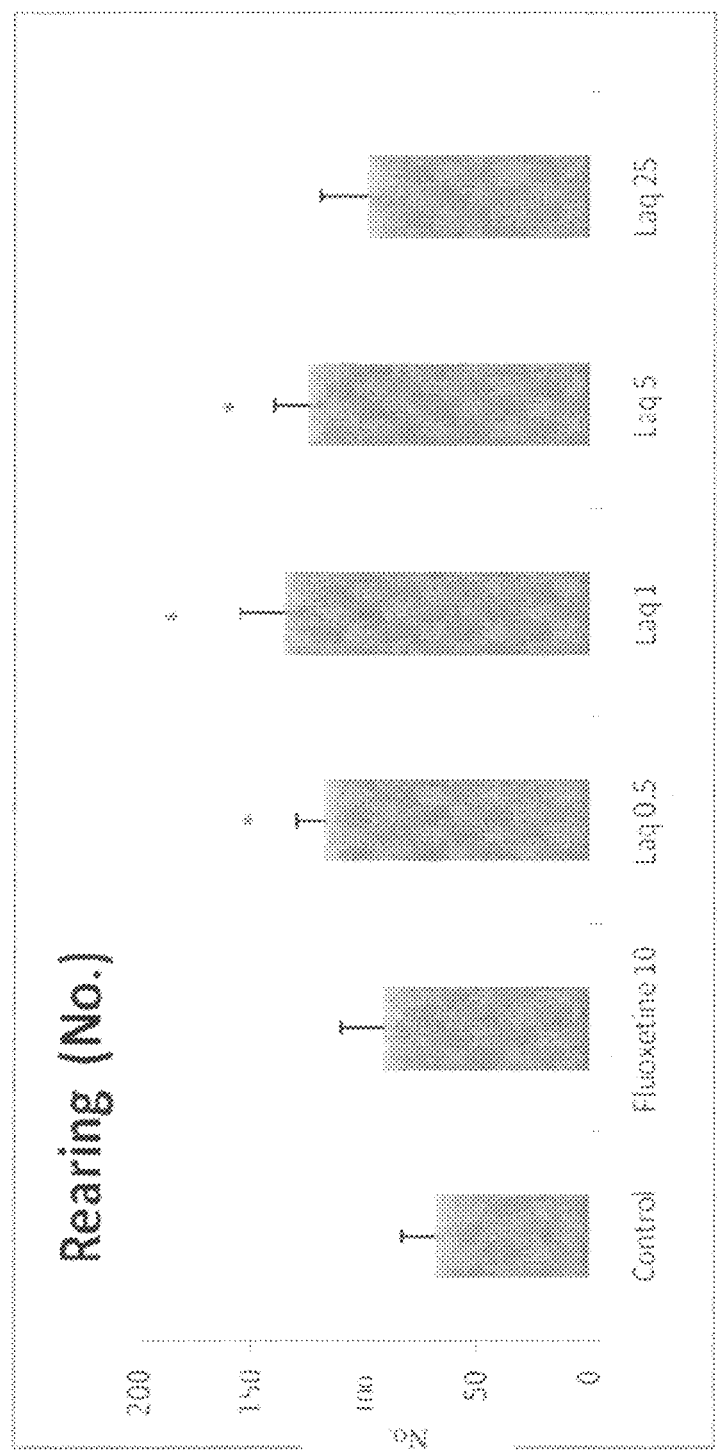
Figure 9D:
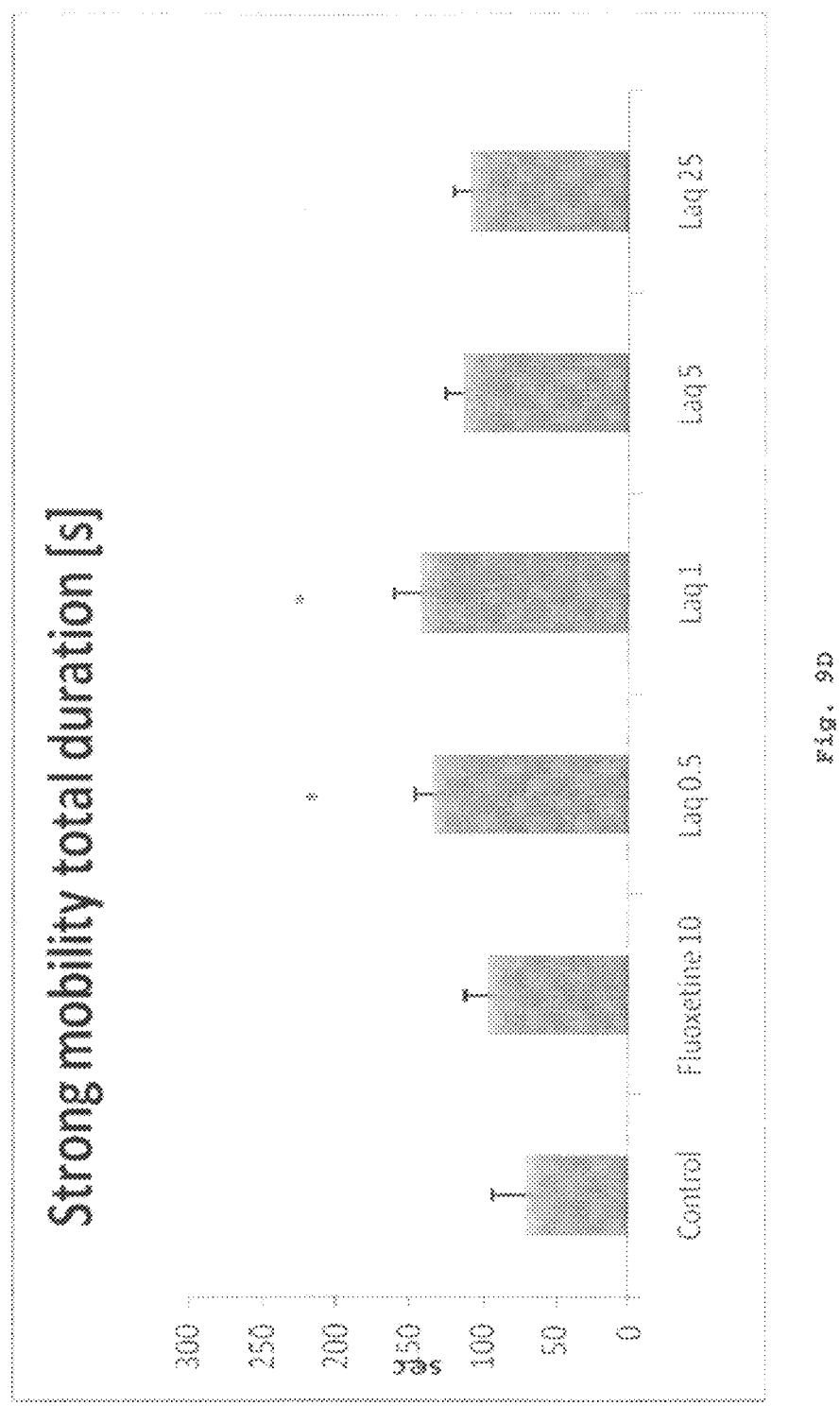
Figure 10A:
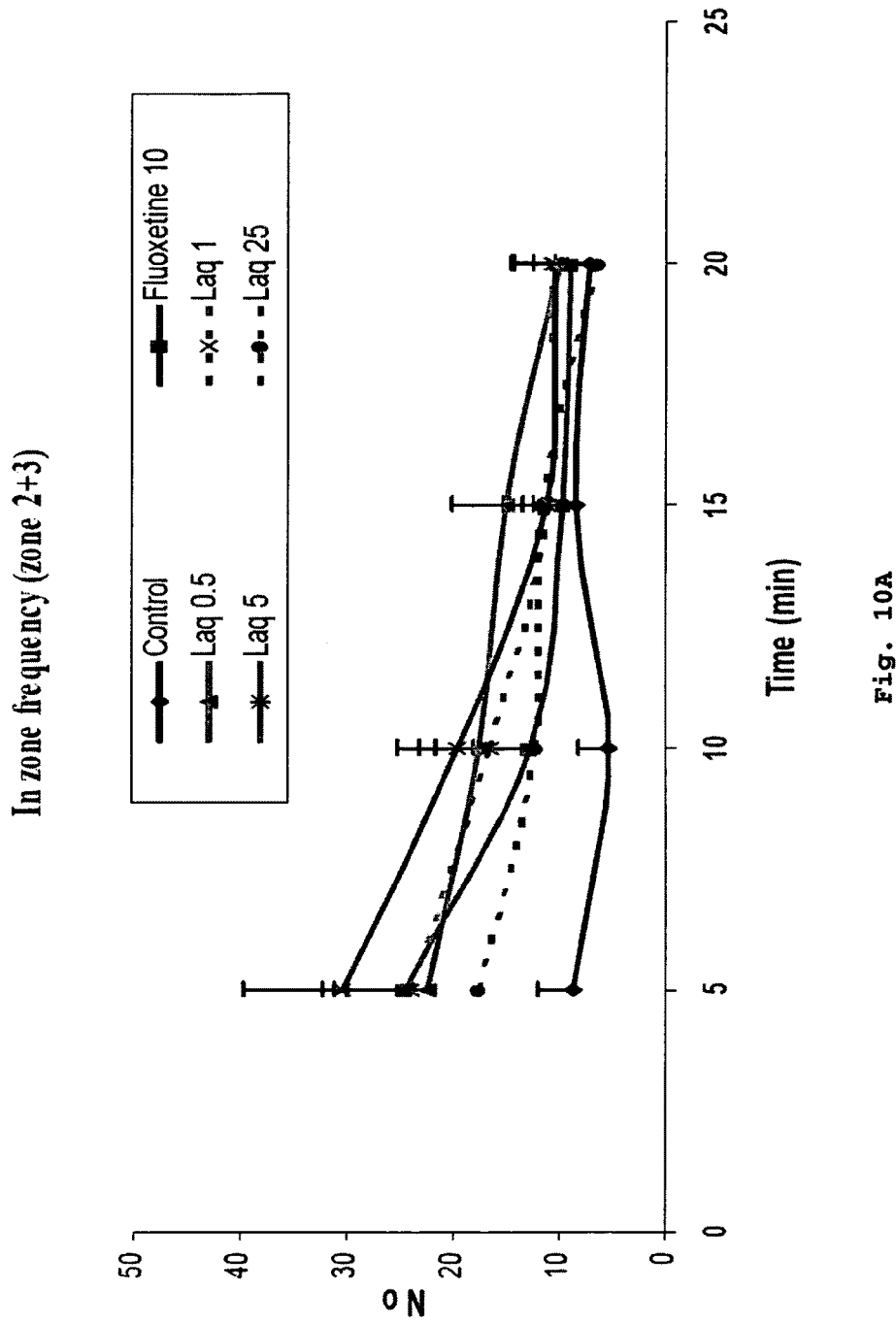
Figure 10B:
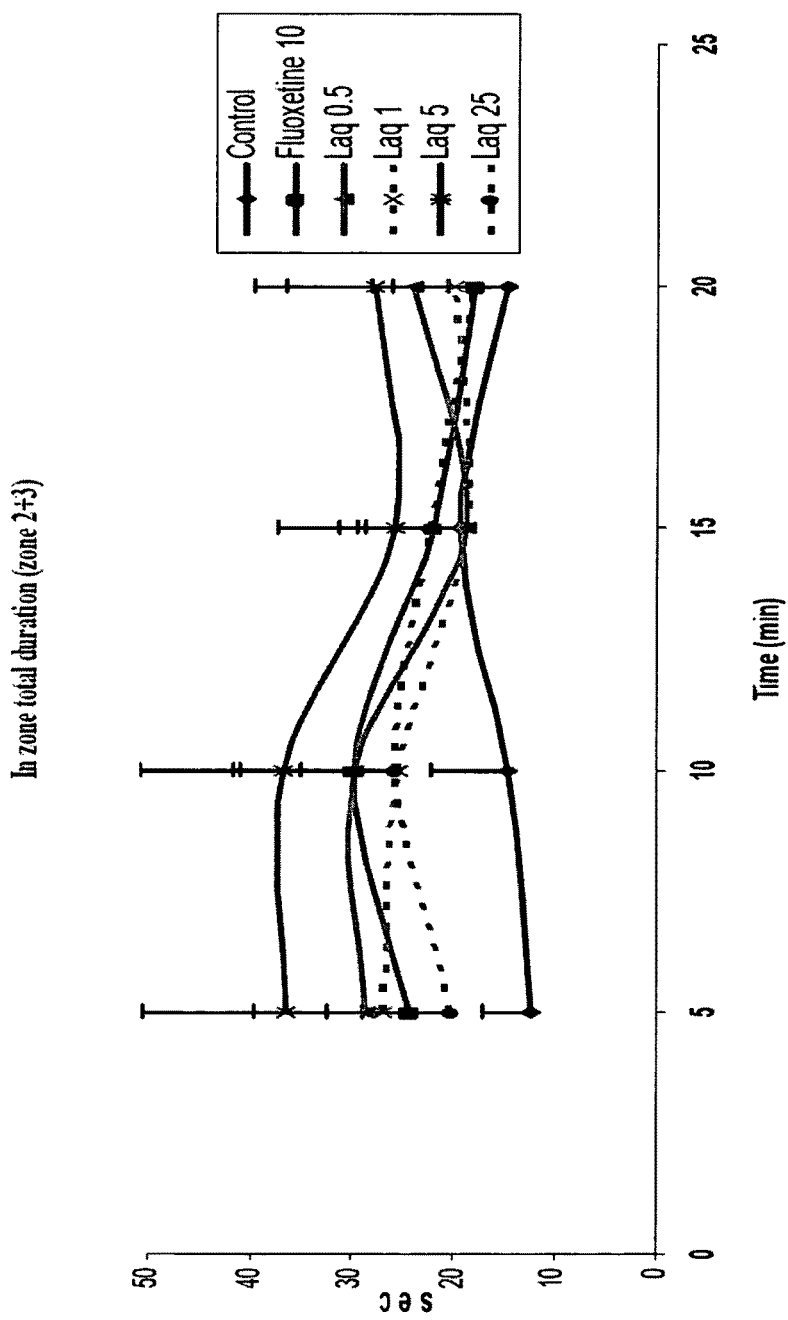
Figure 10C:
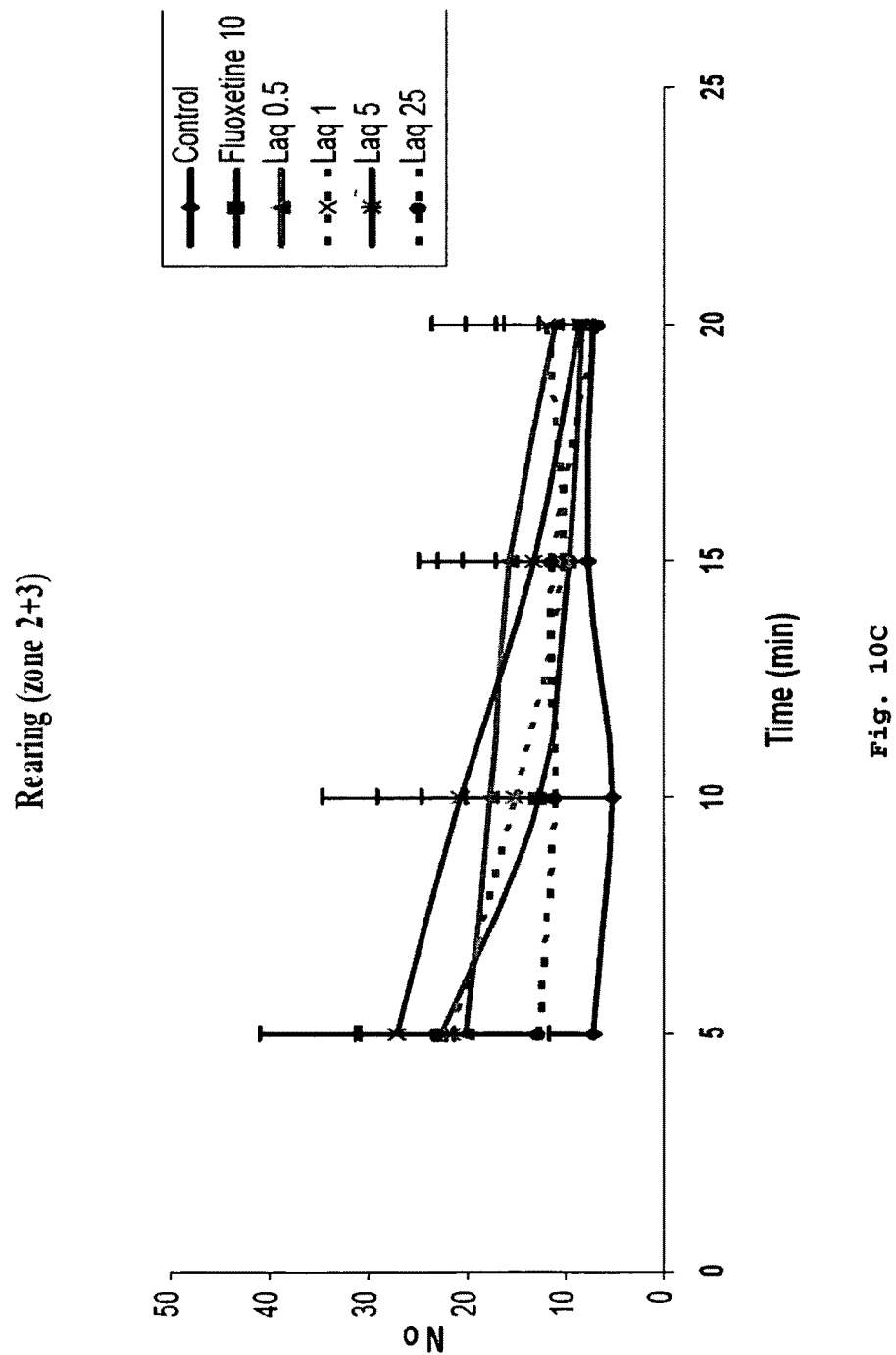
Figure 11A:
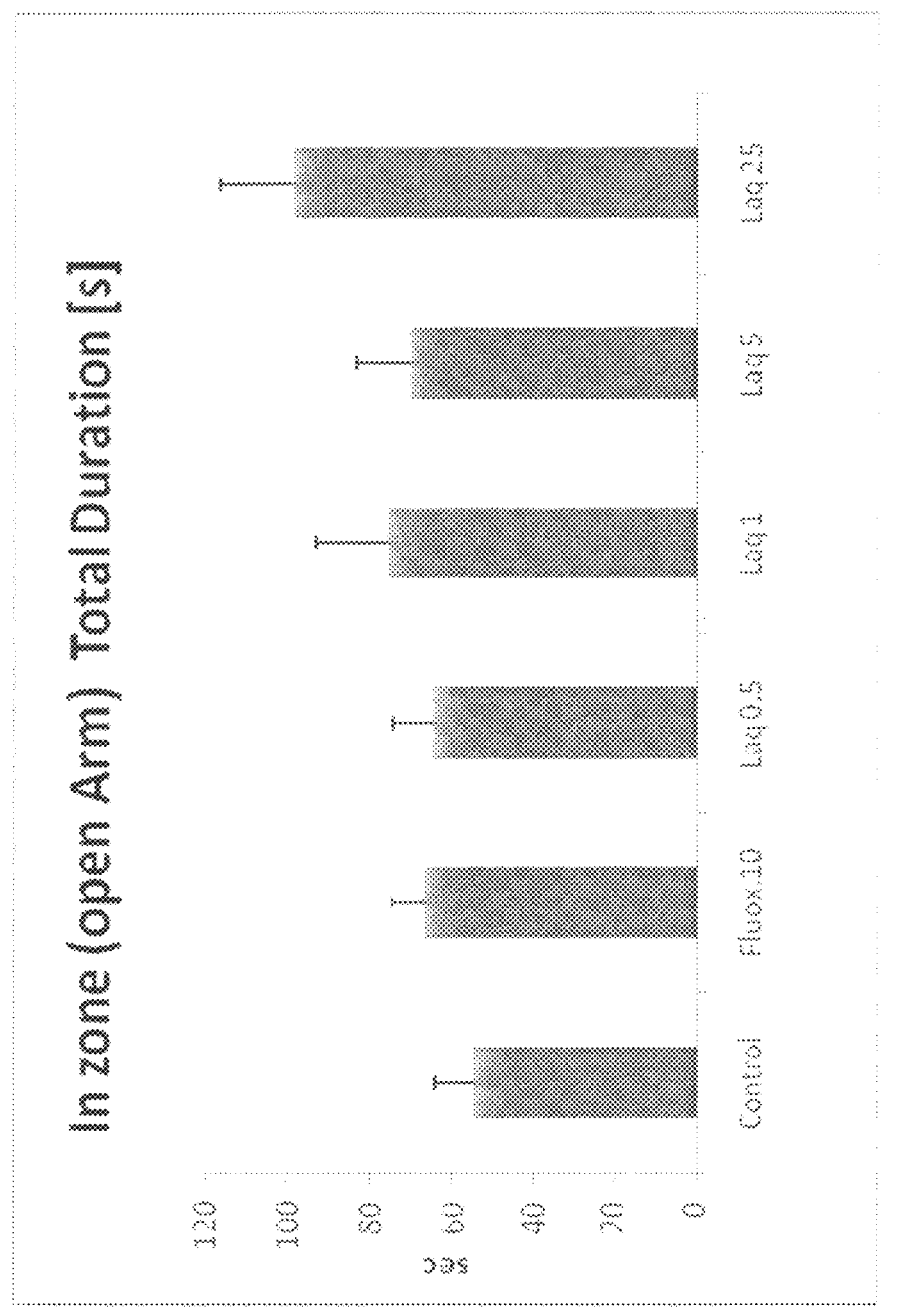
Figure 11B:
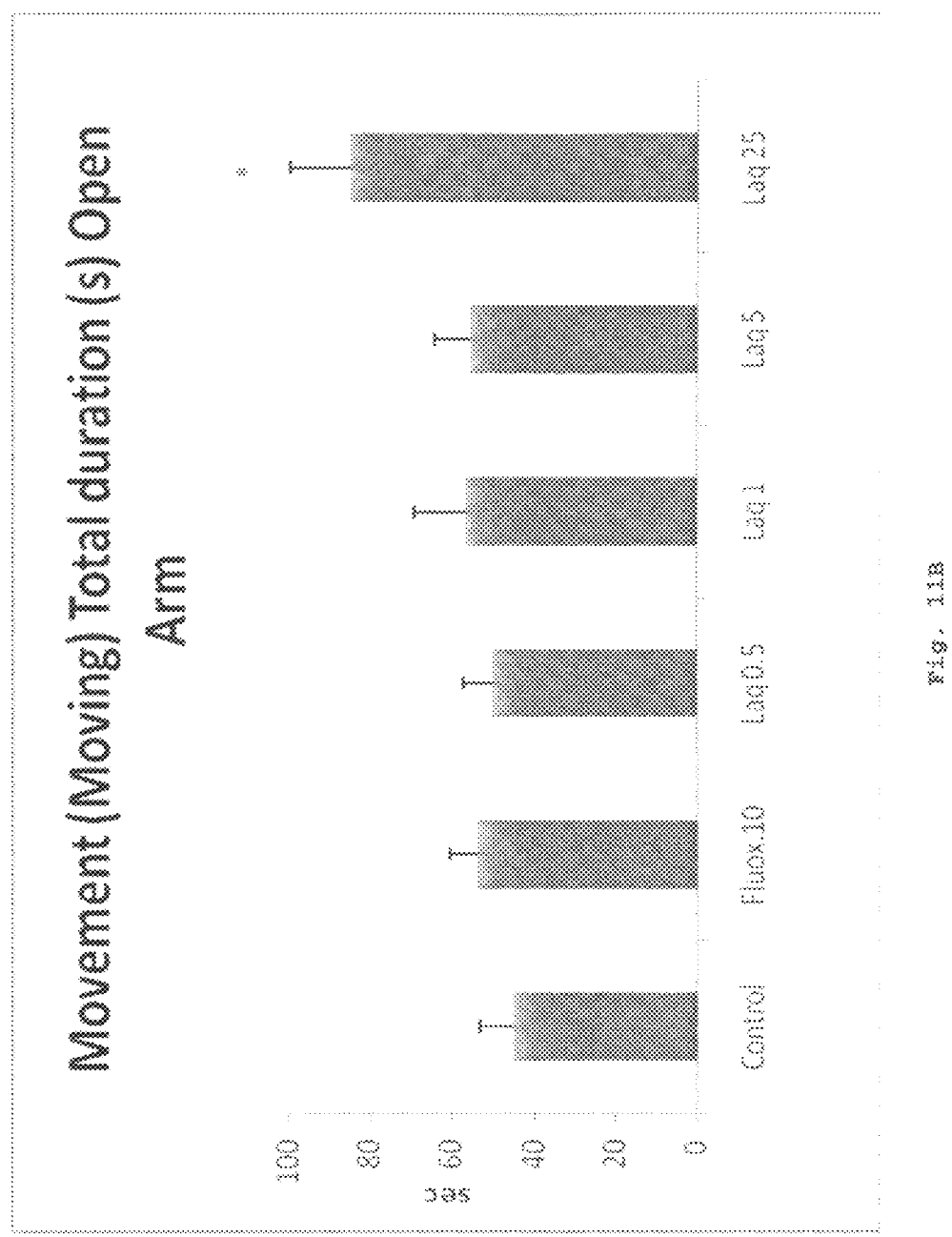
Figure 11C:
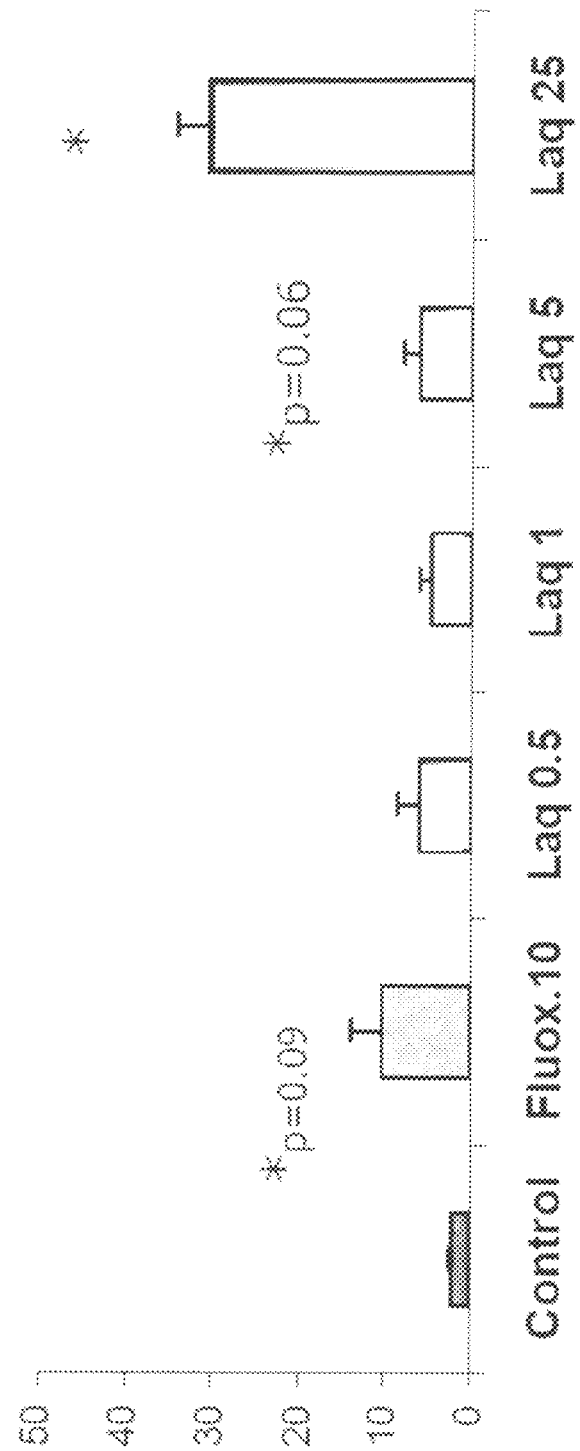
Figure 11D:
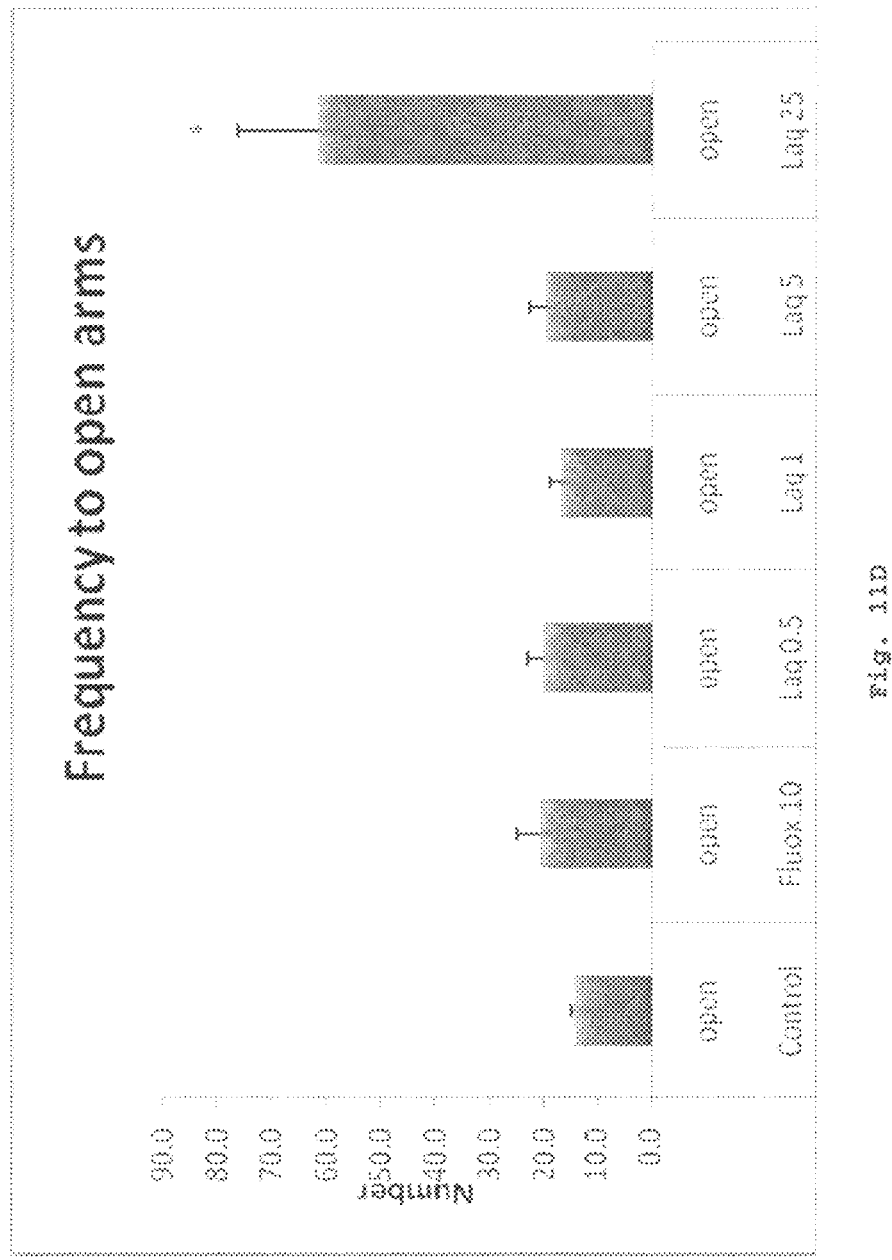

FIG. 8: Shows Open Field Test—anxiety parameter results (in zone 2+3) conducted in Example 3.1. (N=5/group) Laquinimod (1-25/kg/dx3d po) showed tendency toward anxiolytic effect with animals being more active in the center (zones 2+3). 1 mg/kg was shown to be most potent dose.

8C: Effect of Laquinimod (1; 5; 10; 25 mg/kg, po; −90 min) and Fluoxetine (10 mg/kg, po; −90 min) and combination in the Open field test on Rearing Frequency on BALB/c mice [20 min]

FIG. 9: Shows Open Field Test—motility parameter results conducted in Example 3.2. (N=5/group; *p<0.05 vs. cont) Laquinimod (0.5-25 mg/kg/dx3d po) induced a slight increase in motility (0.5-5 mg/kg) in the open field in Balb/c mice.

FIG. 10: Shows Open Field Test—anxiety parameter results (in zones 2+3) conducted in Example 3.2. Laquinimod (0.5-25 mg/kg/dx3d po) shows significant anxiolytic effect with animals showing more activity in the center (zones 2+3). Both fluoxetine and laquinimod (0.5-5 mg/kg) showed significant anxiolytic effect vs. the control. The most potent dose was laquinimod at 5 mg/kg.

FIG. 11: Shows Elevated Plus Maze model results conducted in Example 4.1. Laquinimod (5 and 25 mg/kg/dx3d po) showed significant anxiolytic effect. Laquinimod showed a dose dependent increase in activity on the open arm. The dose at 25 mg/kg p.o. was the most active.

Figure 12A:
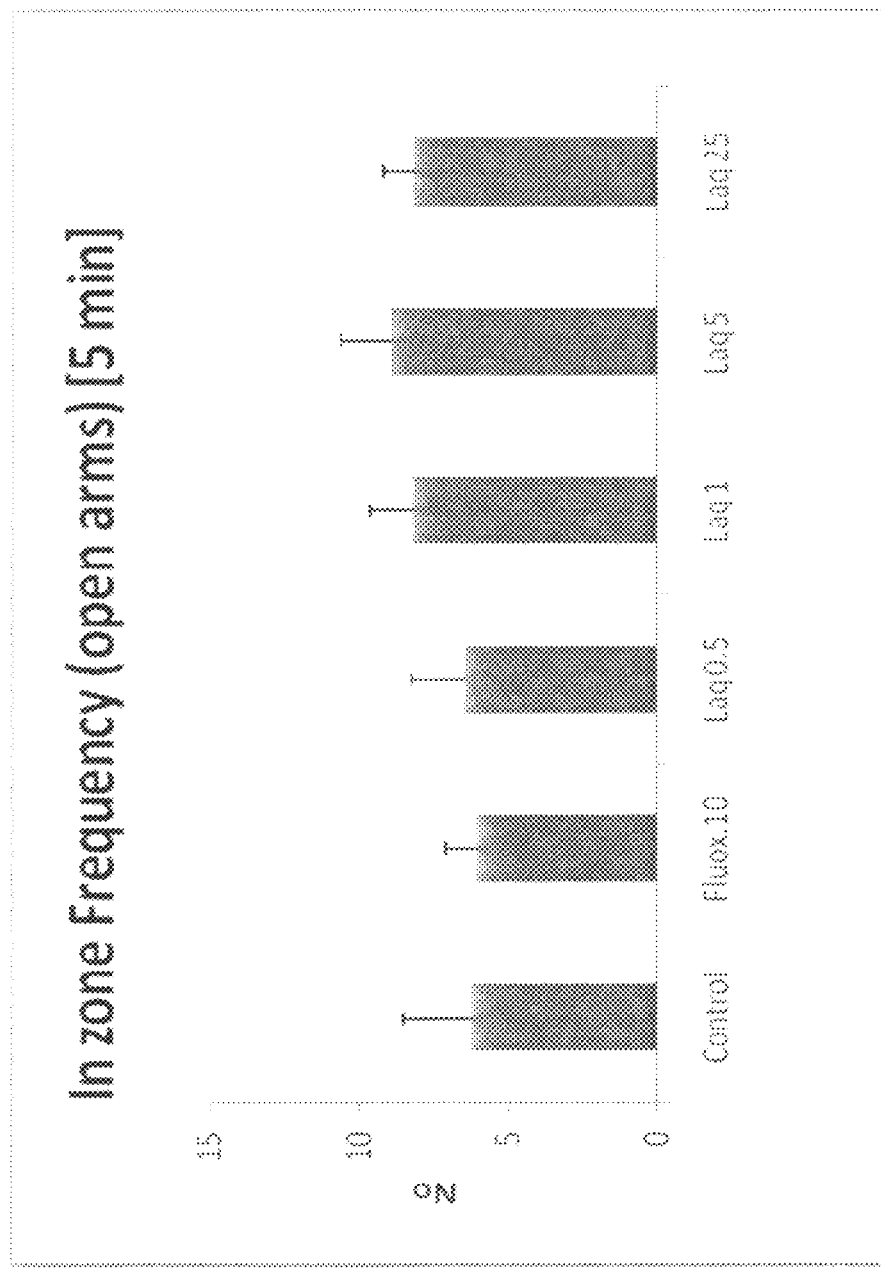
Figure 10B:
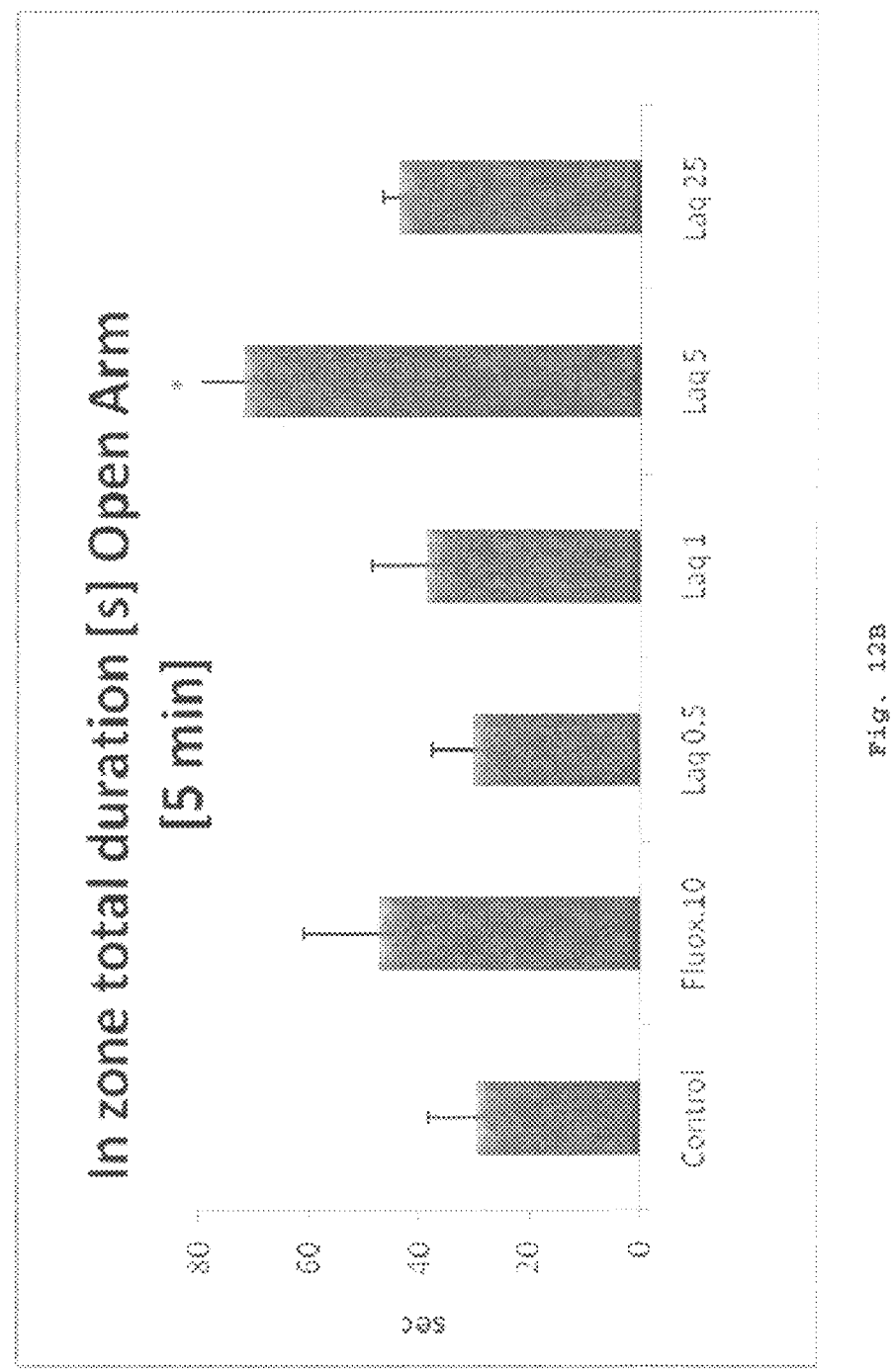
Figure 12C:
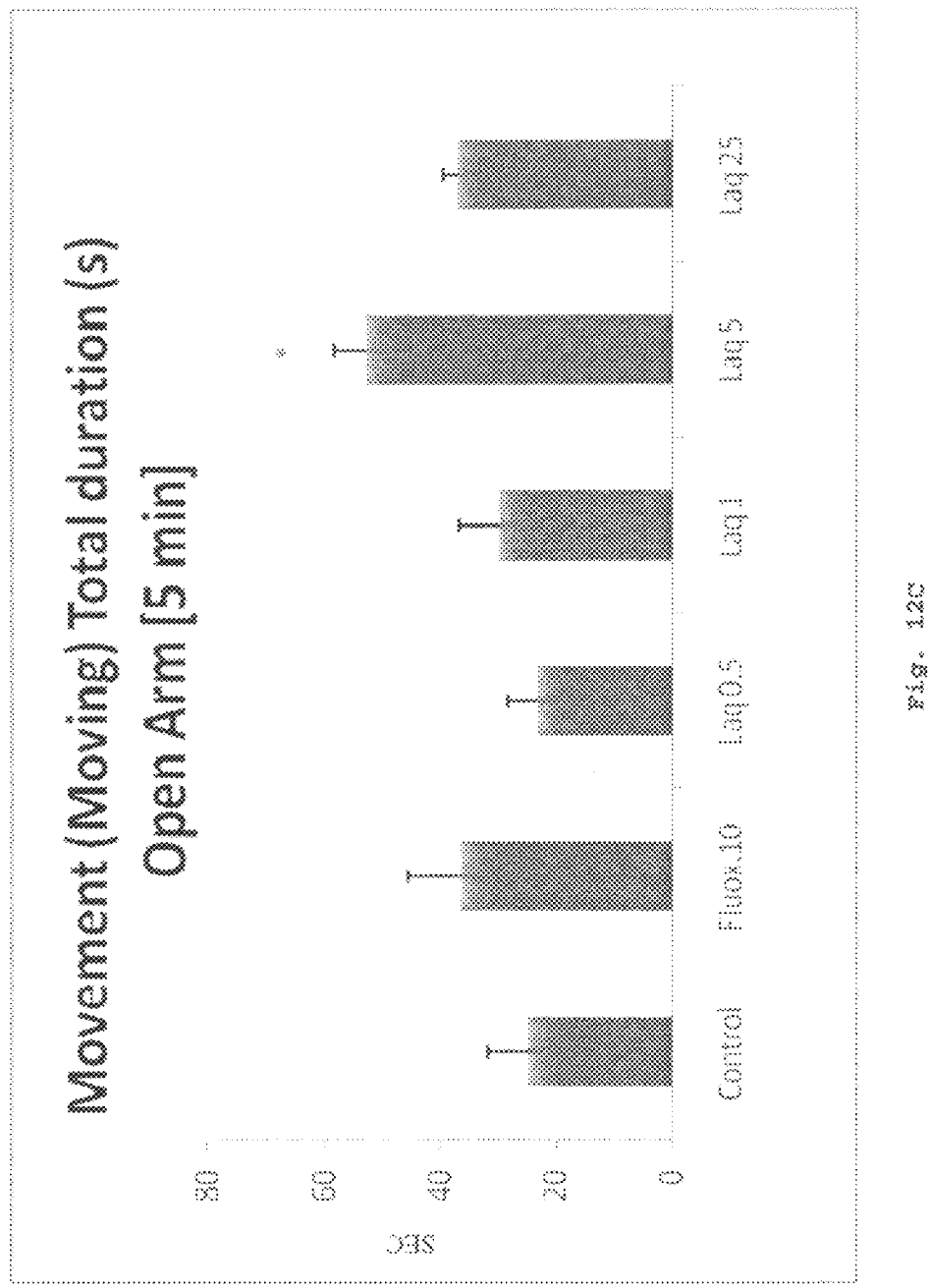
Figure 12D:
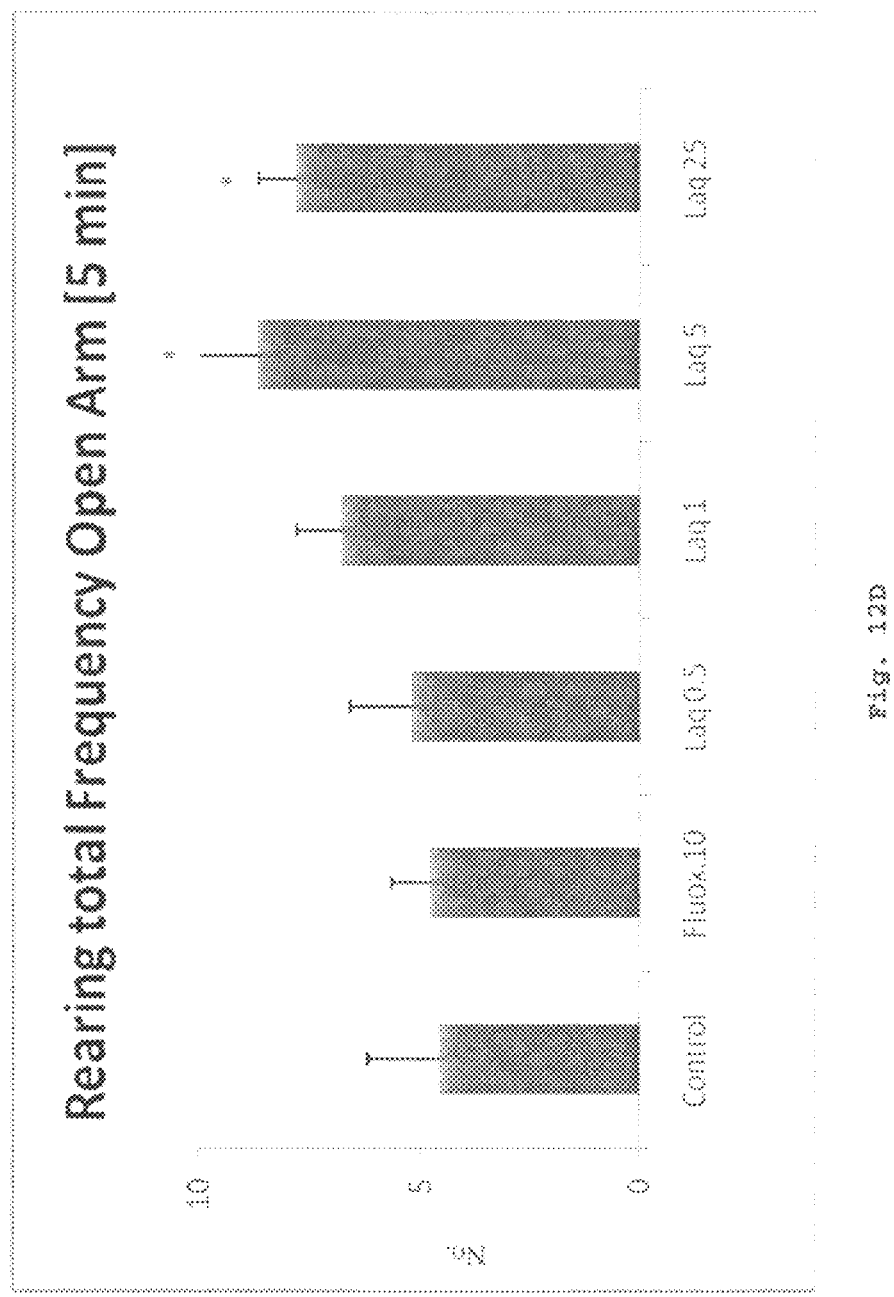

FIG. 12: Shows Elevated Plus Maze model results conducted in Example 4.2. (Open arm parameters in Balb/c mice—5 min; N=5/group) Laquinimod (5-25 mg/kg/dx3d po) showed significant anxiolytic effect.

DETAILED DESCRIPTION OF THE INVENTION

This application provides for a method of increasing brain-derived neurotrophic factor (BDNF) serum level in a human subject comprising periodically administering to the subject an amount of laquinimod or pharmaceutically acceptable salt thereof effective to increase BDNF serum level in the human subject.

In one embodiment, the amount of laquinimod or pharmaceutically acceptable salt thereof is administered to the human subject once daily. In another embodiment, the periodic administration continues for at least 3 days.

In one embodiment, the amount of laquinimod administered is 0.1 mg/day-40.0 mg/day. In another embodiment, the amount of laquinimod administered is 0.6 mg/day. In another embodiment, the amount of laquinimod is administered orally.

In one embodiment, the subject is suffering from a BDNF-related disease. In another embodiment, the BDNF-related disease is Parkinson's disease, Huntington's disease, amyotrophic lateral sclerosis, a depressive disorder, an anxiety disorder, retinitis pigmentosa, erectile dysfunction, a memory disorder, Rett syndrome, Alzheimer's disease, bipolar disorder or acute mania.

In an embodiment, the depressive disorder is depression, depression in cancer patients, depression in Parkinson's disease patients, postmyocardia infarction depression, depression in patients with human immunodeficiency virus (HIV), subsyndromal symptomatic depression, depression in infertile women, pediatric depression, major depression, single episode depression, recurrent depression, child abused-induced depression, post-partum depression, DSM-IV major depression, treatment-refractory major depression, severe depression, psychotic depression, post-stroke depression, neuropathic pain, manic depressive illness including manic depressive illness with mixed episodes and manic depressive illness with depressive episodes, seasonal affective disorder, bipolar depression BP I, bipolar depression BP II, or major depression with dysthymia.

In another embodiment, the anxiety disorder is generalized anxiety, panic disorder, phobia, post traumatic stress disorder, obsessive compulsive disorder, separation anxiety, or childhood anxiety.

In one embodiment, the method further comprises periodically administering to the subject an amount of a second BDNF-increasing agent.

In one embodiment, the amount of the second BDNF-increasing agent when taken alone is not effective to increase BDNF serum level in the subject.

In one embodiment, the administration of the laquinimod substantially precedes the administration of the second BDNF-increasing agent. In another embodiment, the administration of the second BDNF-increasing agent substantially precedes the administration of the laquinimod.

In one embodiment, the effect on the subject is greater than the effect on a subject treated with the second BDNF-increasing agent alone. In another embodiment, the increase in BDNF serum level in the subject is greater than the increase in BDNF serum level in a subject treated with the second BDNF-increasing agent alone.

In one embodiment, the pharmaceutically acceptable salt of laquinimod is laquinimod sodium.

In one embodiment, the diagnosis of the subject prior to administration excluded multiple sclerosis, insulin-dependent diabetes mellitus, systemic lupus erythematosus, rheumatoid arthritis, inflammatory bowel disease, psoriasis, asthma, atherosclerosis, stroke and Alzheimer's disease.

This application also provides for a method for treating a human subject suffering from a BDNF-related disease selected from the group consisting of Parkinson's disease, Huntington's disease, amyotrophic lateral sclerosis, depressive disorders, anxiety disorders, retinitis pigmentosa, erectile dysfunction, memory disorders, Rett syndrome, Alzheimer's disease, bipolar disorder and acute mania comprising periodically administering laquinimod or a pharmaceutically acceptable salt thereof in an amount effective to treat the human subject.

This application also provides for use of laquinimod in the manufacture of a medicament for increasing BDNF serum level in a human subject.

This application also provides for a pharmaceutical composition comprising an amount of laquinimod effective for use in increasing BDNF serum level in a human subject.

This application also provides for a pharmaceutical preparation comprising an amount of laquinimod and an amount of a second BDNF-increasing agent effective for use in increasing BDNF serum level in a human subject.

For the foregoing embodiments, each embodiment disclosed herein is contemplated as being applicable to each of the other disclosed embodiment.

Terms

As used herein, and unless stated otherwise, each of the following terms shall have the definition set forth below.

As used herein, "administering to the subject" means the giving of, dispensing of, or application of medicines, drugs, or remedies to a subject to relieve or cure a pathological condition. Oral administration is one way of administering the instant compounds to the subject.

As used herein, "BDNF" means brain-derived neurotrophic factor, a neurotrophic factor belonging to the neurotrophin family of growth factors.

As used herein, a "BDNF-related disease" is a disease in which a patient suffering from the disease has BDNF serum levels which are lower than those of a corresponding healthy individual and/or a disease in which the elevation of BDNF in a patient suffering from the disease can be associated with amelioration of the disease or of symptoms thereof.

As used herein, a "BDNF-increasing agent" is any agent which directly or indirectly elevates BDNF level in a subject. For example, a BDNF-increasing agent can be riluzole or an antidepressant such as fluoxetine. As used herein, the term "agent" includes any molecule, compound, protein, peptide, polypeptide, nucleic acid, antibody, or drug or any combination thereof.

As used herein, an "amount" or "dose" of laquinimod as measured in milligrams refers to the milligrams of laquinimod acid present in a preparation, regardless of the form of the preparation. For example, 0.6 mg of laquinimod means the amount of laquinimod acid in a preparation is 0.6 mg, regardless of the form of the preparation. Thus, when in the form of a salt, e.g. a laquinimod sodium salt, the weight of the salt form necessary to provide a dose of 0.6 mg laquinimod would be greater than 0.6 mg due to the presence of the additional salt ion, but would be a molar equivalent amount.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat a symptom of a disorder or disease without causing undue adverse side effects. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

A "salt" is salt of the instant compounds which have been modified by making acid or base salts of the compounds. The term "pharmaceutically acceptable salt" in this respect, refers to the relatively non-toxic, inorganic and organic acid or base addition salts of compounds of the present invention.

A pharmaceutically acceptable salt of laquinimod can be used. A pharmaceutically acceptable salt of laquinimod as used in this application includes lithium, sodium, potassium, magnesium, calcium, manganese, copper, zinc, aluminum and iron. Salt formulations of laquinimod and the process for preparing the same are described, e.g., in U.S. Patent Application Publication No. 2005-0192315 and PCT International Application Publication No. WO 2005/074899, which are hereby incorporated by reference into this application.

As used herein, to "treat" or "treating" encompasses, e.g., inducing inhibition, regression, or stasis of the disorder and/or disease. As used herein, "inhibition" of disease progression or disease complication in a subject means preventing or reducing the disease progression and/or disease complication in the subject.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

A dosage unit as used herein may comprise a single compound or mixtures of compounds thereof. A dosage unit can be prepared for oral dosage forms, such as tablets, capsules, pills, powders, and granules.

Laquinimod can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit can be in a form suitable for oral administration. Laquinimod can be administered alone but is generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents flow-inducing agents, and melting agents.

Specific examples of the techniques, pharmaceutically acceptable carriers and excipients that may be used to formulate oral dosage forms of the present invention are described, e.g., in U.S. Patent Application Publication No. 2005/0192315, PCT International Application Publication Nos. WO 2005/074899, WO 2007/047863, and WO/2007/146248, each of which is hereby incorporated by reference into this application.

General techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

It is understood that where a parameter range is provided, all integers within that range, and tenths thereof, are also provided by the invention. For example, "0.1 mg –40.0 mg" includes 0.1 mg, 0.2 mg, 0.3 mg, 0.4 mg, etc. up to 40.0 mg.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Clinical Trial Showing Effect of Laquinimod on BDNF Levels in Human Subjects Afflicted With Relapsing Remitting Multiple Sclerosis A study was initiated in relapsing remitting multiple sclerosis (RRMS) patients using laquinimod, 0.6 mg daily, in the form of the sodium salt, in an oral, once-daily tablet formulation. The study was a multinational, multicenter, randomized, double-blind, parallel-group, placebo controlled study assessing the efficacy, tolerability and safety of two doses of laquinimod in subjects with RRMS. Eligible subjects were randomized into the following three groups:
1. 0.6 mg of laquinimod per os (p.o.) once daily;
2. 0.3 mg of laquinimod per os (p.o.) once daily; and
3. Matching placebo, per os (p.o.) once daily. Subjects must meet the following inclusion criteria to be included in the study:
1. a confirmed MS diagnosis as defined by the McDonald criteria;
2. a RRMS disease course;
3. at least one documented relapse n the 12 months prior to screening;
4. at least one Gadolinium-enhanced lesion on their screening MRI scan;
5. ambulatory with a Kurtzke EDSS score of 1.0-5.0 (Converted);
6. between 18-50 years of age inclusive;
7. relapse-free and off corticosteroids or ACTH for at least 30 days prior to the MRI scan at screening;
8. relapse-free and off corticosteroids between screening and randomization;
9. women of child-bearing potential practiced a reliable method of birth control;
10. willing and able to comply with the protocol requirements for the duration of the study; and
11. able to give signed, written and informed consent prior to entering the study.

Subjects meeting any one of the following exclusion criteria were excluded from the study:
1. suffered from any form of progressive MS;
2. use of immunosuppressive or cytotoxic treatments within 6 months prior to the screening visit (including azathioprine, cyclophosphamide and methotrexate);
3. use of experimental drugs, and/or participation in drug clinical studies within the 6 months prior to screening;
4. previous treatment with immunomodulators (including IFN-β1a and 1b, glatiramer acetate, laquinimod and IVIG) within the 2 months prior to screening;
5. use of potent inhibitors of CYP3A4, for example, oral ketoconazole and erythromycin within 2 weeks prior to baseline visit;
6. previous use of amiodarone;
7. use of fluoxetine one month prior to baseline visit;
8. use of substrates of CYP1A2 such as theophylline and warfarin within 2 weeks prior to screening;
9. previous treatment with cladribine within the last 2 years prior to screening visit;
10. subjects for whom potential immunosuppression would be contraindicated, for example, Hepatitis B/C or HIV.
11. previous total body irradiation or total lymphoid irradiation;
12. chronic corticosteroid treatment (30 or more consecutive days) within the 2 months prior to screening;
13. pregnancy or breastfeeding;
14. subjects with a clinically significant or unstable medical or surgical condition that would preclude safe and complete study participation as determined by medical history, physical exams, ECG, abnormal laboratory tests and chest X-ray.
15. inability to give informed consent, or to complete the study, or if the subject is considered by the investigator to be, for any reason, an unsuitable candidate for the study;
16. a known history of sensitivity to Gd; or
17. inability to successfully undergo MRI scanning.

The study duration was 40 weeks and consisted of 2 periods: 4 weeks of screening period (week −4 [ screening] to week 0 [ baseline]) and 36 weeks of double blind treatment (week 0 [ baseline] to week 36 [ termination]).

Subjects were evaluated at study sites at weeks −4, 0, 4, 8, 12, 16, 20, 24, 28, 32 and 36. Samples for inflammatory markers were collected at all visits between 0 and 36 weeks.

BDNF concentration in serum was measured in patients in the placebo group (102 patients were in the group) and in the 0.6 mg laquinimod group (106 patients were in the group) at week 0 (V0), week 12 (v3) and week 36 (V9). The analysis of BDNF content in the plasma was performed using the sandwich ELISA method. The concentration of BDNF in serum is expressed in terms of pg/mL.

Results

The results in the tables below represent mean BDNF levels in both the laquinimod 0.6 mg/day group and the placebo group.

Baseline Values (at V0)

TABLE 1

Mean and Std Deviations

| Level | Number | Mean | Std Dev | Std Err Mean | Err Lower 95% | Err Upper 95% |
|---|---|---|---|---|---|---|
| Placebo | 95 | 14110.7 | 6432.61 | 659.97 | 12800 | 15421 |
| Laquinimod 0.6 mg | 96 | 13892.7 | 7267.89 | 741.78 | 12420 | 15365 |

TABLE 2 t Test
Laquinimod 0.6 mg-Placebo - Assuming unequal variances

| Difference | −218.0 | t-Ratio | −0.2196 |
|---|---|---|---|
| Std Err Dif | 922.9 | DF | 186.6984 |
| Upper CL Dif | 1740.7 | Prob > \|t\| | 0.8264 |
| Lower CL Dif | −2176.7 | Prob > t | 0.5868 |
| Confidence | 0.95 | Prob < t | 0.4132 |

Week 12 Values (at V3)

TABLE 3

Mean and Std Deviations

| Level | Number | Mean | Std Dev | Std Err Mean | Err Lower 95% | Err Upper 95% |
|---|---|---|---|---|---|---|
| Placebo | 96 | 13073.9 | 5712.02 | 582.98 | 11916 | 14231 |
| Laquinimod 0.6 mg | 100 | 15519.6 | 7204.47 | 720.45 | 14090 | 16949 |

TABLE 4 t Test
Laquinimod 0.6 mg-Placebo - Assuming unequal variances

| Difference | 2445.70 | t-Ratio | 2.638935 |
|---|---|---|---|
| Std Err Dif | 926.77 | DF | 187.3752 |
| Upper CL Dif | 4273.95 | Prob > \|t\| | 0.0090* |
| Lower CL Dif | 617.44 | Prob > t | 0.0045* |
| Confidence | 0.95 | Prob < t | 0.9955 |

Week 36 Values (at V9)

TABLE 5

Mean and Std Deviations

| Level | Number | Mean | Std Dev | Std Err Mean | Err Lower 95% | Err Upper 95% |
|---|---|---|---|---|---|---|
| Placebo | 92 | 12783.6 | 6017.17 | 627.33 | 11538 | 14030 |
| Laquinimod 0.6 mg | 92 | 15335.8 | 6699.89 | 698.51 | 13948 | 16723 |

TABLE 6 t Test
Laquinimod 0.6 mg-Placebo - Assuming unequal variances

| | | | |
|---|---|---|---|
| Difference | 2552.21 | t-Ratio | 2.718403 |
| Std Err Dif | 938.86 | DF | 179.9376 |
| Upper CL Dif | 4404.81 | Prob > \|t\| | 0.0072* |
| Lower CL Dif | 699.61 | Prob > t | 0.0036* |
| Confidence | 0.95 | Prob < t | 0.9964 |

Starting from V3 there is a statistically significant elevation of BDNF (at Confidence Level of 95%) between the placebo group and the laquinimod 0.6 mg group. The difference was also statistically significant at V9.

Laquinimod is effective in experimental autoimmune encephalomyelitis (aEAE) model, and is currently being tested in MS patients (on phase III clinical trial) thus suggesting the possibility of its use in treatment of multiple sclerosis (MS). Laquinimod is also effective in increasing BDNF levels in the patients.

The ability of laquinimod to increase BDNF levels is unexpected. A per se connection between treatment of MS and increase in BDNF levels has not been established. Not all agents which are effective in treating MS are effective in elevating BDNF levels. A recent study showed that treatment with interferon-β 1a and immunoglobulins, even after 12 months, and even in MS patients benefitting from the treatment, did not show an increase in plasma BDNF levels (Sarchielli, 2007). The finding that laquinimod elevates BDNF levels in patients after only 12 weeks of treatment is unexpected.

Example 2

Laquinimod Shows Antidepressant Activity in Mice Models—the Forced Swim Test (FST)

Depression and anxiety disorders are burdensome conditions with lifetime prevalence rates of approximately 7-20%. Animal models are indispensable tools in the search to identify new antidepressant drugs. Various paradigms have been developed and are instrumental in detecting the antidepressant-like potential of novel compounds in preclinical settings (Cryan, 2002; Ganbarana, 2001).

The Forced Swim Test (FST) is one of the most widely used tools for screening antidepressant activity pre-clinically. The acute test was first described by Porsolt et al (1977).

The test is based on the observation that rats and mice develop an immobile posture when placed in an inescapable cylinder of water. This behavior is considered to be a behavioral despair as opposed to active form of coping with stressful conditions. An antidepressant will reduce immobility and increase motivated behavior of the rodent to escape from the despaired conditions. This is evidenced by increase in time of swimming, distance moved, velocity and attempts to climb the walls (strong mobility).

FST is considered a screening tool with high reliability and predictive validity. The test can be performed in mice and rats.

In example 2.1 and 2.2 described below, the FST was conducted in male mice (Balb/c Harlan IL) after 3 days of drug administration, 90 minutes after the last drug administration. Round glass cylinders 18 cm diameter and 20 cm depth were used. Water temperature was 24-28° C. Motivated behavior was defined by immobility, swimming and strong mobility.

Immobility in the animals was defined by activity lower than 10% movement of the center of gravity of the animal as determined by the Noldus system. Swimming was defined by the distance and the velocity of the animal, and climbing was related to strong mobility (movement of center of gravity more than 30%). Animals were released in the cylinder for 6 min and scoring was performed in the last 4 min after 2 min of adaptation.

All results were analyzed by the Noldus (Holland) system including a camera and software for animal behavior analyses.

Example 2.1

Balb/c mice were divided to 6 groups (5/group) and administered daily for 3 days laquinimod (1, 5, 10 and 25 mg/kg per os in the form of laquinimod sodium solution via gavage), fluoxetine (positive control 10 mg/kg per os) or vehicle. On the third day, 90 min following administration, mice were exposed to the forced swim test. Behavior was video recorded and analyzed using Ethovision software (Noldus Holland). The result is shown in FIG. 4.
Conclusion:

The results show that laquinimod showed a significant antidepressant activity as expressed by the increased mobility and reduced immobility at 1 mg/kg, and a trend to significance at higher doses (Laquinimod at 25 mg/kg). In this experiment, the positive control fluoxetine did not show significant effect, possibly due to non optimal conditions of time and dose.

Example 2.2

Balb/c mice were divided to 6 groups (5 mice/group) and administered laquinimod daily for 3 days with (0.5, 1, 5 and 25 mg/kg p.o. in the form of laquinimod sodium solution via gavage), fluoxetine (positive control 10 mg/kg po) or vehicle. On the third day, 90 minutes following administration, mice were exposed to the forced swim test. Behavior was video recorded and analyzed using Ethovision software (Noldus Holland). The result is shown in FIG. 5.
Conclusion:

The results show that laquinimod showed a significant antidepressant activity as expressed by the increased mobility and reduced immobility at 5 and 25 mg/kg. The positive control fluoxetine showed a trend to the same activity. This is possibly due to non optimal conditions of time and dose.

Example 3

Laquinimod Shows Anxiolytic Activity in Mice Models—the Open Field Test

Anxiety disorders are blanket terms covering several different forms of abnormal and pathological fear and anxiety. Current psychiatric diagnostic criteria recognize a wide variety of anxiety disorders. Recent surveys have found that as many as 18% of Americans may be affected by one or more of them (Kessler et al). The disorders are divided to several classes including: Generalized Anxiety, Panic disorders, Phobias, Post Traumatic Stress Disorders (PTSD), Obsessive Compulsive Disorder (OCD), Separation Anxiety and Childhood Anxiety.

Chronically administered antidepressant drugs, particularly selective serotonin (5-HT) reuptake inhibitors (SSRIs), are clinically effective in the treatment of all anxiety disorders, including post traumatic stress disorder (PTSD) and obsessive compulsive disorder (OCD). While the clinical effectiveness of traditional anxiolytics, such as benzodiazepines (BDZs), is limited to generalized anxiety disorder or acute panic attacks (Borsini et al). Thus the potential anxiolytic effect of antidepressants is of great relevance.

The Open Field Test—Exploratory locomotor activity used in Examples 3.1 and 3.2 described below is one of the most popular in evaluation of animals' behavior. It tests both motility parameters and anxiety (Prut et al). An individual mouse is placed in a novel plexiglass arena of 50×50 cm the floor of which is divided into 3 digital zones: the outer peripheral zone 1, the medial zone 2 and the most central zone 3. The animal behavior in the open field is recorded by videotaping for 20 min and is analyzed subsequently digitally using Noldus software for animal behavior. The measurements include general motility (distance moved, velocity and strong mobility) and anxiety parameters (including frequency of visits to the central area, time spent in the inner field, and number of rearing events in the center). The more the animal stays and performs in the center, the less anxious it is.

Example 3.1

Balb/c male mice were divided to 6 groups (5/group) and administered laquinimod (1, 5, 10 and 25 mg/kg p.o. in the form of laquinimod sodium solution via gavage), fluoxetine (positive control 10 mg/kg po) or vehicle daily for 3 days. On the third day, 90 min following administration, mice were exposed to the open field for 20 min. Behavior was video recorded and analyzed using Ethovision software (Noldus Holland). The results with respect to motility parameters are shown in FIG. 6. The results with respect to anxiety parameters are shown in FIGS. 7 and 8.

Conclusion:

Motility Parameters—Laquinimod and fluoxetine did not modify significantly the motility parameters in the field in this model.

Anxiety Parameters (Zone 2)—Animals treated with laquinimod and with fluoxetine tended to perform more in the center in terms of frequency, time spent, distance moved and number of rearings. The results show 1 mg/kg and 5 mg/kg were the most potent.

Anxiety Parameters (Zones 2 and 3)—Animals treated with laquinimod tended to perform more in the center as evidenced by time spent, distance moved and number of rearings. The results show 1 mg/kg was the most potent dosage of laquinimod in this experiment.

This model shows that laquinimod shows anxiolytic effects.

Example 3.2

Balb/c male mice were divided to 6 groups (5/group) and administered laquinimod (0.5, 1, 5 and 25 mg/kg p.o. in the form of laquinimod sodium solution via gavage), fluoxetine (positive control 10 mg/kg po) or vehicle daily for 3 days. On the third day, 90 min following administration, mice were exposed to the open field test for 20 minutes. Behavior was video recorded and analyzed using Ethovision software (Noldus Holland). The motility parameter results are shown in FIG. 9. The anxiety parameter results are shown in FIG. 10.

Conclusion:

Motility Parameters—Laquinimod (0.5-25 mg/kg/dx3d po) induced a slight increase in motility (0.5-5 mg/kg) in the open field in Balb/c mice.

Anxiety Parameters—Animals treated with laquinimod (0.5-5 mg/kg po) and with Fluoxetine (10 mg/kg po) performed significantly more in the center as judged by frequency, time spent and number of rearings. 5 mg/kg was the most potent.

This model shows that laquinimod shows anxiolytic effects.

Example 4

Laquinimod Shows Anxiolytic Activity in Mice Models—Elevated Plus Maze (EPM)

The EPM model used in Examples 4.1 and 4.2 described below utilizes the natural fear of rodents to avoid open and elevated places. The apparatus consists of a plus-maze with two enclosed and two opposite open arms, elevated above the floor. Naive animals spend only about 30% of the test time on open arms, while treatment with benzodiazepines significantly increases open-arm exploration (Pellow et al). This is one of the most widely used models to study effects of anxiety-like behavior.

The maze consisted of two opposing open arms (40×10 cm) and two opposing closed arms (40×10 cm, with 40 cm walls) on a platform 50 cm above the ground. Mice were placed in the center square (10×10 cm) facing an open arm and videotaped during a 5 min exploration. Arm entries and duration were scored when all four paws enter the arm.

Example 4.1

Balb/c male mice were divided to 6 groups (5/group) and administered laquinimod (0.5, 1, 5 and 25 mg/kg p.o. in the form of laquinimod sodium solution via gavage), fluoxetine (positive control 10 mg/kg po) or vehicle daily for 3 days. On the third day, 90 min following administration, mice were exposed to the EPM for 5 minutes. Mice were placed in the center square (10×10 cm) facing an open arm and videotaped during a 5 minute exploration. Arm entries and duration was scored when all four paws enter the arm. Behavior was video recorded and analyzed using Ethovision software (Noldus Holland). The results are shown in FIG. 11.

Conclusion:

Mice treated with laquinimod show anxiolytic activity in a dose dependent manner. Maximal effect was obtained with the dose of 25 mg/kg po.

Example 4.2

Balb/c male mice were divided to 6 groups (5/group) and administered laquinimod (0.5, 1, 5 and 25 mg/kg p.o. in the form of laquinimod sodium solution via gavage), fluoxetine (positive control 10 mg/kg po) or vehicle daily for 3 days.

On the third day, 90 min following administration, mice were exposed to the EPM for 5 min.

Behavior was video recorded and open arms parameters were analyzed using Ethovision software (Noldus Holland). The results are shown in FIG. 12.

Conclusion:

Mice treated with laquinimod show anxiolytic activity in a dose dependent manner. Maximal effect was obtained with 5-25 mg/kg po.

REFERENCES

1. PCT International Application Publication No. WO 2007/047863, published Apr. 26, 2007, international filing date Oct. 18, 2006.
2. PCT International Application Publication No. WO 2007/146248, published Dec. 21, 2007, international filing date Jun. 12, 2007.
3. Acheson, A, et al. (1995). "A BDNF autocrine loop in adult sensory neurons prevents cell death". *Nature*, 374 (6521):450-3.
4. Alonsa, M, et al. (2005) "Endogenous BDNF is required for long-term memory formation in the rat parietal cortex". *Learning & Memory*, 12:504-510.
5. Amaral, M D, et al. (2007) "TRPC channels as novel effectors of BDNF signaling: Potential implications for Rett syndrome". *Pharmacol Ther*, 113(2):394-409.
18. Borsini F, et al. (2002) "Do animal models of anxiety predict anxiolytic-like effects of antidepressants?"*Psychopharmacology*. 163:121-41.
6. Caffe Romeo, A, et al. (2001) "A combination of CNTF and BDNF rescues rd photoreceptors but changes rod differentiation in the presence of RPE in retinal explants". *Investigative Opthalmology & Visual Science*, 42:275-82.
7. Chesselet, M F (2003) "Dopamine and Parkinson's disease: is the killer in the house?" *Molecular Psychiatry*, 8:369-370.
8. Ciammola, A, et al. (2007) "Low brain-derived neurotrophic factor (BDNF) levels in serum of Huntington's disease patients". *Am J Med Gent Part B*, 144b:574-577.
9. Cryan J F, et al. (2002) "Assessing antidepressant activity in rodents: recent developments and future needs". *Trend in Pharmacological Science*. 23:238-45.
10. Gambarana, C., et al. (2001) "Animal models for the study of antidepressant activity". *Brain Res. Protocol.* 7:11-20.
11. Howells, D W, et al. (2000) "Reduced BDNF mRNA expression in the Parkinson's disease substantia nigra". *Experimental Neurology*, 166(1):127-135.
12. Huang, E J and Reichardt, L F (2001) "Neurotrophins: roles in neuronal development and function". *Annu. Rev. Neurosci*, 24:677-736.
13. Hyman, C. et al., (1991) "BDNR is a neurotrophic factor for dopaminergic neurons of the substantia nigra". *Nature*, 350(6315):230-2.
14. Katoh-Semba, R, et al. (2002) "Riluzole enhances expression of brain-derived neurotrophic factor with consequent proliferation of granule precursor cells in the rat hippocampus". *FASEB J*, 16:1328-30.
19. Kessler R C, et al. (June 2005) "Prevalence, severity, and comorbidity of 12-month DSM-IV disorders in the National Comorbidity Survey Replication". *Arch. Gen. Psychiatry.* 62(6):617-27.
15. Molteni, R, et al. (2006) "Abstract: Chronic treatment with fluoxetine [Prozac®] up-regulates cellular BDNF mRNA expression in rat dopaminergic regions". *Int J. Neuropsychopharmacol.* 9(3):307-17.
16. Monteggia, L M (2007) "Elucidating the role of brain-derived neurotrophic factor in the brain". *Am J Psychiatry,* 164:1790.
20. Pellow S, et al. (1985) "Validation of open:closed arm entries in an elevated plus-maze as a measure of anxiety in the rat". *J Neurosci Methods.* 14:149-167.
21. Porsolt R. D., et al. (1977) "Behavioral despair in mice: a primary screening test for antidepressants". *Arch. Int. Pharmacodyn. Ther.* 229: 327-336.
22. Prut L, and Belzung C. (2003) "The open field as a paradigm to measure the effects of drugs on anxiety-like behaviors: a review". *Eur J. Pharmacol.* 463:3-33.
17. Riviere, M (1998) "An analysis of extended survival in patients with amyotrophic lateral sclerosis treated with riluzole". *Arch Neurol,* 55:526-8.
18. Sarchielli, P, et al. (2007) "Production of Brain-derived neurotrophic factor by mononuclear cells of patients with multiple sclerosis treated with glatiramer acetate, interferon-pβ 1a, and high doses of immunoglobulins". *Multiple Sclerosis,* 13:313-331.
19. Sen, S, et al. (2008) "Serum brain-derived neurotrophic factor, depression, and antidepressant medications: meta-analyses and implications". *Biol Psychiatry,* 64:527-532.
20. Snider, et al., (1989) "Neurotrophic molecules". *Ann Neurol,* 26(4):489-506.
21. Tramontina, J F, et al. (2009) "brain-derived neurotrophic factor serum levels before and after treatment for acute mania". *Neuroscience Letters,* 452:111-3.

What is claimed is:

1. A method for treating a human subject suffering from Huntington's disease, consisting essentially of periodically administering an amount of laquinimod or a pharmaceutically acceptable salt thereof effective to treat the human subject.
2. The method of claim 1, wherein the amount of laquinimod or pharmaceutically acceptable salt thereof is administered to the human subject once daily.
3. The method of claim 1, wherein the periodic administration continues for at least 3 days.
4. The method of claim 1, wherein the amount of laquinimod or pharmaceutically acceptable salt thereof administered is 0.1 mg/day-40.0 mg/day.
5. The method of claim 4, wherein the amount of laquinimod or pharmaceutically acceptable salt thereof administered is 0.6 mg/day.
6. The method of claim 1, wherein the amount of laquinimod or pharmaceutically acceptable salt thereof administered is 0.1 mg/day-0.6 mg/day.
7. The method of claim 1, wherein the amount of laquinimod or pharmaceutically acceptable salt thereof is administered orally.
8. The method of claim 1, wherein the pharmaceutically acceptable salt of laquinimod is laquinimod sodium.
9. The method of claim 6, wherein the amount of laquinimod or pharmaceutically acceptable salt thereof is administered orally.
10. The method of claim 9, wherein the pharmaceutically acceptable salt of laquinimod is laquinimod sodium.

* * * * *